US010877034B2

(12) United States Patent
Moulder et al.

(10) Patent No.: US 10,877,034 B2
(45) Date of Patent: Dec. 29, 2020

(54) MEANS AND METHODS FOR DETERMINING RISK OF TYPE-1 DIABETES BY SERUM PROTEIN BIOMARKERS

(71) Applicant: TURUN YLIOPISTO, Turun yliopisto (FI)

(72) Inventors: Robert Moulder, Turku (FI); Santosh Bhosale, Turku (FI); David Goodlett, Baltimore, MD (US); Harri Lähdesmäki, Espoo (FI); Olli Simell, Raisio (FI); Riitta Lahesmaa, Turku (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 635 days.

(21) Appl. No.: 15/319,515

(22) PCT Filed: Jun. 18, 2015

(86) PCT No.: PCT/FI2015/050448
§ 371 (c)(1),
(2) Date: Dec. 16, 2016

(87) PCT Pub. No.: WO2015/193552
PCT Pub. Date: Dec. 23, 2015

(65) Prior Publication Data
US 2017/0160276 A1 Jun. 8, 2017

(30) Foreign Application Priority Data
Jun. 18, 2014 (FI) .................................. 20140186

(51) Int. Cl.
G01N 31/00 (2006.01)
G01N 33/53 (2006.01)
G01N 33/564 (2006.01)
G01N 33/92 (2006.01)

(52) U.S. Cl.
CPC .......... *G01N 33/564* (2013.01); *G01N 33/92* (2013.01); *G01N 2333/47* (2013.01); *G01N 2333/4713* (2013.01); *G01N 2333/4716* (2013.01); *G01N 2333/76* (2013.01); *G01N 2333/775* (2013.01); *G01N 2560/00* (2013.01); *G01N 2570/00* (2013.01); *G01N 2800/042* (2013.01); *G01N 2800/50* (2013.01); *G01N 2800/60* (2013.01)

(58) Field of Classification Search
None
See application file for complete search history.

(56) References Cited

U.S. PATENT DOCUMENTS

2012/0177660 A1 7/2012 She et al.

FOREIGN PATENT DOCUMENTS

| EP | 1 840 573 A1 | 10/2007 |
|----|---|---|
| WO | WO 2010/141469 A2 | 12/2010 |
| WO | WO 2013/106851 A2 | 7/2013 |
| WO | WO 2014/015217 A1 | 1/2014 |

OTHER PUBLICATIONS

Langley et al. (Sci. Transl. Med. Jul. 24, 2013; 5(195); pp. 133).*
Langley etal. Supplemental Data, Jul. 24, 2013.*
Langley et al. (Sci. Transl. Med. Jul. 24, 2013; 5(195); pp. 1-33) (Year: 2013).*
Atikinson et al., "Type 1 diabetes," The Lancet (Jan. 4, 2014), vol. 383, pp. 69-82.
Daka et al., "Inverse association between serum insulin and sex hormone-binding globulin in a population survey in Sweden," Endorine Connections (2013), vol. 2, pp. 18-22.
Dieplinger et al., "Analytical characterization and clinical evaluation of an enzyme-linked immunosorbent assay for measurement of afamin in human plasma," Clinica Chimica Acta (2013), vol. 425, pp. 236-241.
Dornan et al., "Alleles of the Second Component of Complement (C2) in Insulin-Dependent Diabetes Mellitus," Hum. Hered. (1981), vol. 31, pp. 211-213.
Galler et al., "Elevated serum levels of adiponectin in children, adolescents and young adults with type 1 diabetes and the impact of age, gender, body mass index and metabolic control: a longitudinal study," European Journal of Endocrinology (2007), vol. 157, pp. 481-489.
Gokulakrishnan et al., "Serum Adiponectin Helps to Differentiate Type 1 and Type 2 Diabetes Among Young Asian Indians." Diabetes Technology & Therapeutics (2013), vol. 15, No. 8, pp. 695-701.
Hanifi-Moghaddam et al., "Altered chemokine levels in individuals at risk of Type 1 diabetes mellitus," Diabetic Medicine (2006), vol. 23, pp. 156-163.
Kotite et al., "Human apoC-IV: isolation, characterization, and immunochemical quantification in plasma and plasma lipoproteins," J. Lipid Res. (2003), vol. 44, pp. 1387-1394.
Kronenberg et al., "Plasma Concentrations of Afamin are Associated With the Prevalence and Development of Metabolic Syndrome,"Circ. Cardiovasc. Genet. (2014), vol. 7, pp. 822-829.
Lu et al., "Proteomic analysis of retinopathy-related plasma biomarkers in diabetic patients," Archives of Biochemistry and Biophysics (2013), vol. 529, pp. 146-156.
McGuire et al., "Screening newborns for candidate biomarkers of type 1 diabetes," Archives of Physiology and Biochemistry (2010), vol. 116, No. 4-5, pp. 227-232.
Moulder et al., "Serum Proteomes Distinguish Children Developing Type 1 Diabetes in a Cohort With HLA-Conferred Susceptibility," Diabetes (Jun. 2015), vol. 64, pp. 2265-2278.

(Continued)

*Primary Examiner* — Lisa V Cook
(74) *Attorney, Agent, or Firm* — Birch, Stewart, Kolasch & Birch, LLP

(57) ABSTRACT

The present invention relates to methods for predicting a risk of a subject for Type 1 diabetes (T1D) on the basis of expression levels of protein markers in a sample obtained from the subject. The present invention also relates to in vitro kits for use in said methods.

6 Claims, 10 Drawing Sheets

(56) References Cited

OTHER PUBLICATIONS

Rocha et al., "Testicular function during adolescence in boys with type 1 diabetes mellitus (T1D): absence of hypogonadism and differences in endocrine profile at the beginning and end of puberty," Pediatric Diabetes (2014), vol. 15, pp. 198-205.
Rowe et al., "Increased Complement Activation in Human Type 1 Diabetes Pancreata," Diabetes Care (2013), vol. 36, pp. 3815-3817.
Van Dam et al., "Steroids in Adult Men With Type 1 Diabetes," Diabetes Care (2003), vol. 26, pp. 1812-1818.
Zhi et al., "Proteomic Technologies for the Discovery of Type 1 Diabetes Biomarkers," J. Diabetes Sci. Technol. (2010), vol. 4, No. 4, pp. 933-1002.

\* cited by examiner

MEANS AND METHODS FOR DETERMINING RISK OF TYPE-1 DIABETES BY SERUM PROTEIN BIOMARKERS

CROSS-REFERENCE TO RELATED APPLICATIONS

This application is a National Stage of International Application No. PCT/FI2015/050448 filed on Jun. 18, 2015 and claims priority to Finnish Application No. 20140186 filed in Finland on Jun. 18, 2014. The entire contents of all of the above applications are hereby incorporated by reference.

FIELD OF THE INVENTION

The present invention relates to the field of molecular diagnostics. More specifically the present invention relates to means and methods for predicting a risk of a subject for Type 1 diabetes (T1D).

BACKGROUND OF THE INVENTION

The measurement of islet cell autoantibodies is currently the principle means of identifying an emerging threat in developing Type 1 diabetes. The risks associated with the appearance of islet antibodies have been evaluated in depth, and overall the appearance of multiple biochemically defined autoantibodies correlates with progression to disease irrespective of genetic risk group or autoantibody combination. T1D is generally diagnosed at the point when the majority of the insulin producing beta cells in the pancreas have been destroyed, at which stage the patient is dependent on insulin supplements for the rest of their life. Methods to establish risk and potential onset are thus needed to gain insight in the disease etiology and design potential treatment/prevention strategies.

Proteomic analyses in the study of T1D have previously mostly addressed differences in sera from diabetic patients and non-diabetic subjects. Whilst in-depth comparisons of proteins in samples from healthy subjects and patients with T1D have distinguished the diseased state, the identification of changes preceding this aggressive autoimmune disease is important for disease prediction and prevention. Such markers could be used in the evaluation of risks and preventative treatments.

BRIEF DESCRIPTION OF THE INVENTION

The present disclosure is directed to methods and kits that useful for identifying the risk that an individual, particularly an individual having a HLA-conferred risk for type 1 diabetes, will develop type 1 diabetes (T1D). The risk can be determined based on amounts of one or more of the protein markers disclosed herein.

In one aspect, the present disclosure is directed to a method of predicting, determining and/or monitoring a risk of and/or progression towards Type 1 Diabetes (T1D) in an individual. The method comprises the steps of a) determining a protein marker profile in a sample obtained from the individual, said profile comprising:
  i) PROF1 and FLNA,
  ii) SHBG,
  iii) AFAM and APOC4, or
  iv) IBP2, ADIPO, and CO2, b) comparing the determined protein marker profile and a corresponding control profile, and c) responsive to the comparison, determining a prediction corresponding to a relative risk of the individual developing T1D or a stage of progression towards T1D.

In some embodiments, the profile of i) further comprises one or more protein markers selected from the group consisting of VASP, CFL1, ACTB, TAGL2 and TMSB4X. In some other embodiments, the profile of ii) further comprises one or more protein markers selected from the group consisting of CO8G, ZPI, BTD, CO5, and THBG. In some further embodiments, the profile of iv) further comprises one or both protein markers selected from SHBG, CO8G. In some still further aspects, any of the marker profiles set forth above may further comprise any one or more protein markers selected from those listed in Table 4 and/or Table 5.

According to some embodiments, the above-defined profiles of i) to iii) are used to predict the risk of T1D prior to seroconversion.

In some embodiments, the individual whose risk for developing T1D has a HLA-conferred risk for T1D.

In another aspect, the present disclosure is directed to an in vitro screening kit comprising one or more testing agents for testing a biological sample for a protein marker profile indicative of a risk of developing T1D, wherein said profile comprises:
  i) PROF1 and FLNA;
  ii) SHBG;
  iii) AFAM and APOC4; or
  iv) IBP2, ADIPO, and CO2.

In some embodiments, the kit comprises one or more testing agents which recognize the protein markers of profile i) and one or more further testing agents which recognize one or more protein markers selected from the group consisting of TAGL2, VASP, CFL1, ACTB, and TMSB4X.

In some other embodiments, the kit comprises one or more testing agents which recognize the protein marker of profile ii) and one or more further testing agents which recognize one or more protein markers selected from the group consisting of CO8G, ZPI, BTD, CO5, and THBG.

In some still other embodiments, the kit comprises one or more testing agents which recognize the protein marker of profile iv) and one or more further testing agents which recognize one or both protein markers selected from the group consisting of SHBG and CO8G.

In some further embodiments, the kit may comprise, in addition to the one or more testing agents set forth above, one or more further testing agents which recognize one or more protein markers listed in Table 4 and/or Table 5.

Other objectives, aspects, embodiments, details and advantages of the present invention will become apparent from the following figures, detailed description, examples, and dependent claims.

BRIEF DESCRIPTION OF THE DRAWINGS

In the following the invention will be described in greater detail by means of preferred embodiments with reference to the attached drawings, in which

FIG. 8A illustrates the receiver-operator characteristic (ROC) curve of the abundance of SHBG throughout the time series (AUC 0.74), while

DETAILED DESCRIPTION OF THE INVENTION

Figure 1:
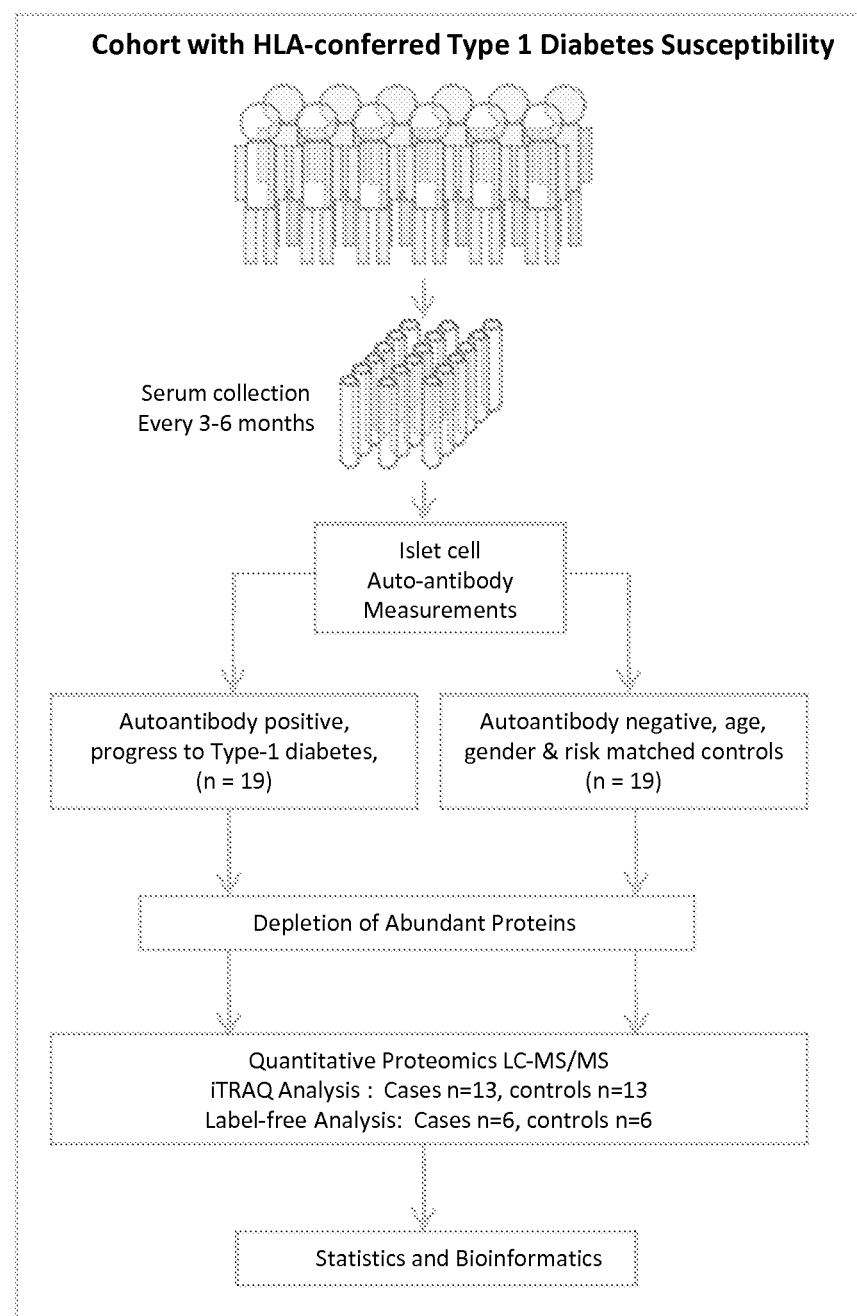
FIG. 1 is a schematic presentation of the study design that depicts the manner in which the discovery was made. Using a prospective longitudinal serum sample collection from children with a HLA-conferred risk for type 1 diabetes, samples were selected on the basis of clinical outcome and the determined levels of type 1 diabetes associated autoantibodies. Serum samples were prepared for proteomics analysis by mass spectrometry. Comparisons were made between children that developed type 1 diabetes and their age, risk and gender matched controls. Two quantitative approaches were employed. Firstly with isotope tagged relative and absolute quantitative (iTRAQ) reagents, secondly using a label free approach.

In some implementations, the present disclosure is directed to methods, proteomic profiles and kits useful for determining or predicting the risk that an individual will develop Type 1 diabetes (T1D), or determining an individual's stage of progression towards T1D, or monitoring or predicting an individual's progression towards T1D. As is described, this risk can be assessed based on the profiles of several panels of protein markers whose applicability, in some embodiments, depends on whether known T1D autoantibodies have been detected.

In some important embodiments, a prediction of an individual's risk of developing T1D can be made prior to any signs of seroconversion. As used herein, the term "seroconversion" refers to the first detection of one or several T1D-associated autoantibodies against beta cell-specific antigens in serum. These include islet cell specific autoantibodies (ICA), insulin autoantibodies (IAA), glutamic acid decarboxylase 65 autoantibodies (GADA), islet antigen-2 autoantibodies (IA-2A), and zinc transporter 8 autoantibodies (ZnT8A). In some embodiments, the following cut-off values may be used for determining the presence or absence of the autoantibodies: ICA≥4 JDFU (Juvenile Diabetes Foundation units), IAA≥3.48 RU (relative units), GADA≥5.36 RU, IA-2A≥0.43 RU, and ZnT8A≥0.61 RU. Seroconversion may occur years, e.g. 1 to 2 years, before clinical diagnosis.

Typically, the individual whose risk for T1D is to be determined is a human subject, preferably a child or an adolescent. In some more preferred embodiments, said subject does not show any signs of seroconversion. As used herein, the terms "subject" and "individual" are interchangeable.

The herein identified predictive proteomic profiles apply in particular to individuals having a Human Leukocyte Antigen (HLA)-conferred risk for T1D. As used herein, the term "HLA-conferred risk for T1D" refers to a predisposition to T1D as determined on the basis of the individual's HLA genotype. In some embodiments, HLA-conferred susceptibility is assigned if the individual carries HLA-DQB1 alleles *02/*0302 or *0302. In the experiments conducted, T1D diagnosed individuals whose risk was HLA-conferred were compared with control subjects with the same susceptibility. Similarly in the implementation of this screen, control and pooled control reference may be employed.

As used herein, the term "proteomic profile" refers to a set of proteins in a biological sample at a given time. A proteomic profile changes continually in response to internal and external events. Thus, a proteomic profile may be used not only to predict an individual's risk of developing a disease at a given time but also to monitor any changes in the prediction or disease status e.g. in response to treatment or dietary or other changes in the individual's lifestyle. The term may be used interchangeably with the terms "protein expression profile", "protein signature", "protein marker profile", and the like, as is evident to a person skilled in the art. Predictive protein markers identified herein include those listed in Table 1.

TABLE 1

Protein markers comprised in various protein marker profiles of the present disclosure

| Protein Abbreviation | Protein name | Protein ID |
|---|---|---|
| ACTB | Actin | P60709 |
| ADIPO | Adiponectin | Q15848 |
| AFAM | Afamin | P43652 |
| APOC4 | Apolipoprotein C-IV | P55056 |
| BTD | Biotinidase | P43251 |
| CFL1 | Cofilin-1 | P23528 |
| CO2 | Complement 2 | P06681 |
| CO5 | Complement 5 | P01031 |
| CO8G | Complement component C8 gamma chain | P07360 |
| FLNA | Filamin-A | P21333 |
| IBP2 | Insulin-like growth factor-binding protein 2 | P18065 |

TABLE 1-continued

Protein markers comprised in various protein marker profiles of the present disclosure

| Protein Abbreviation | Protein name | Protein ID |
|---|---|---|
| PROF1 | Profilin-1 | P07737 |
| SHBG | Sex hormone-binding globulin | P04278 |
| TAGL2 | Transgelin-2 | P37802 |
| THBG | Thyroxine-binding globulin | P05543 |
| TMSB4X | Thymosin beta-4 | P62328 |
| VASP | Vasodilator-stimulated phosphoprotein | P50552 |
| ZPI | Z-dependent protease inhibitor | Q9UK55 |

As used herein, the term "determining a protein marker profile", and the like, refers to detecting, measuring, or otherwise assessing the level, amount, or proportion of one or more protein markers belonging to a given profile. Said determining may give a relative or absolute value representing the amount or level of said marker in a biological sample obtained from an individual whose marker profile and, eventually, the risk of developing T1D, are to be determined.

Suitable biological samples for use in accordance with the present disclosure include, but are not limited to, tissue samples (e.g. pancreatic samples), blood samples including whole blood, serum, plasma, peripheral blood mono-nuclear cells and any purified blood cell type, and urine samples. In essence, any biological protein-containing sample may be used for the present purposes.

The level or amount of a protein marker in a biological sample may be determined by a variety of techniques as is readily apparent to a skilled person. Nonlimiting examples of suitable methods include mass spectrometry-based quantitative proteomics techniques, such as isobaric Tags for Relative and Absolute Quantification reagents (iTRAQ) and label free analysis, as well as selected reaction monitoring (SRM) mass spectrometry. Also, the level or amount of a protein marker may be determined by e.g. an immunoassay, spectrophotometry, an enzymatic assay, an ultraviolet assay, a kinetic assay, an electrochemical assay, a colorimetric assay, a turbidimetric assay, an atomic absorption assay, flow cytometry, or any combination thereof. Further suitable analytical techniques include, but are not limited to, liquid chromatography such as high performance/pressure liquid chromatography (HPLC), gas chromatography, nuclear magnetic resonance spectrometry, related techniques and combinations and hybrids thereof, for example, a tandem liquid chromatography-mass spectrometry (LC-MS).

As used herein, the term "increased expression" refers to an increase in the amount of a protein in a sample as compared with a corresponding control sample. Said increase can be determined qualitatively and/or quantitatively according to standard methods known in the art. The expression is increased if the amount of the protein in the sample is, for instance, at least about 1.5 times, 1.75 times, 2 times, 3 times, 4 times, 5 times, 6 times, 8 times, 9 times, time times, 10 times, 20 times or 30 times the amount of the same protein in the control sample.

As used herein, the term "decreased expression" refers to a decrease in the amount of a protein in a sample as compared with a corresponding control sample. Said decrease can be determined qualitatively and/or quantitatively according to standard methods known in the art. The expression is decreased if the amount of the protein in the sample is, for instance, at least about 1.5 times, 1.75 times, 2 times, 3 times, 4 times, 5 times, 6 times, 8 times, 9 times, time times, 10 times, 20 times or 30 times lower than the amount of the same protein in the control sample.

To determine whether the expression level or the amount of a protein marker is greater than or lower than normal, the normal amount of the protein marker present in a biological sample from a relevant control has to be determined. Once the normal marker amounts are known, the determined marker amounts can be compared therewith and the significance of the difference can be assessed using standard statistical methods. When there is a statistically significant difference between the determined marker amount and the normal amount, there is a significant risk that the tested individual will develop T1D.

In some further embodiments, the levels, amounts or relative ratios of one or more protein markers may be compared with a predetermined threshold value which is indicative of the risk of developing T1D. Statistical methods for determining appropriate threshold values will be readily apparent to those of ordinary skill in the art. The threshold value originates from a relevant control which may be a single individual not affected by T1D or be a value pooled from more than one such individual.

As used herein, the term "relevant control" refers to a control sample, control proteomic profile, or control value, preferably case matched with the individual whose risk for T1D is to be predicted. Case-matching may be made, for instance, on the basis of one of more of the following criteria: age, date of birth, place of birth, gender, predisposition for T1D, HLA status and any relevant demographic parameter. In some embodiments, said control sample or profile consists of a pool of, preferably case-matched, relevant control samples or profiles. In some embodiments, said control prolife or control value has been predetermined prior to predicting a risk of T1D in an individual in accordance with the present disclosure. In some other embodiments, determining said control profile or control value may be comprised as a method step in any of the predictive methods disclosed herein.

Optionally, before to be compared with the control sample, the protein marker levels are normalized using standard methods.

Receiver Operation Characteristic (ROC) curves may be utilized to demonstrate the trade-off between the sensitivity and specificity of a marker, as is well known to skilled persons. The sensitivity is a measure of the ability of the marker to detect the disease, and the specificity is a measure of the ability of the marker to detect the absence of the disease. The horizontal X-axis of the ROC curve represents 1-specificity, which increases with the rate of false positives. The vertical Y-axis of the curve represents sensitivity, which increases with the rate of true positives. Thus, for a particular cutoff selected, the values of specificity and sensitivity may be determined. In other words, data points on the ROC curves represent the proportion of true-positive and false-positive classifications at various decision boundaries. Optimum results are obtained as the true-positive proportion approaches 1.0 and the false-positive proportion approaches 0.0. However, as the cutoff is changed to increase specificity, sensitivity usually is reduced and vice versa.

As used herein, the term "false positive" refers to a test result which classifies an unaffected subject incorrectly as an affected subject, i.e. a subject having or predicted to develop a disease. Likewise, "false negative" refers to a test results which classifies a subject who has or will develop a disease incorrectly as an unaffected subject.

As used herein, the term "true positive" refers to a test result which classifies a subject who has or will develop a disease correctly as a subject having or predicted to develop a disease. Likewise, "true negative" refers to a test result which classifies an unaffected subject correctly as an unaffected.

In accordance with the above, the term "success rate" refers to the percentage-expressed proportion of affected individuals with a positive result, while the terms "false positive rate" and "false detection rate" (FDR) refer to the percentage-expressed proportion of unaffected individuals with a positive result.

The area under the ROC curve, often referred to as the AUC, is a measure of the utility of a marker in the correct identification of disease subjects, i.e. subjects who will develop T1D. Thus, the AUC values can be used to determine the effectiveness of the test. An area of 1.0 represents a perfect test; an area of 0.5 represents a worthless test. A traditional rough guide for classifying the accuracy of a diagnostic or predictive test is the following: AUC values 0.9 to 1.0 represent a test with excellent diagnostic or predictive power, AUC values 0.80 to 0.90 represent a test with good diagnostic or predictive power, AUC values 0.70 to 0.80 represent a test with fair diagnostic or predictive power, AUC values 0.60 to 0.70 represent a test with poor diagnostic or predictive power, and AUC values 0.50 to 0.60 represent a test with failed diagnostic or predictive power.

As described in the experimental part, the present disclosure is based on an analysis on a unique series of prospective serum samples from at-risk children collected in the Finnish Type 1 Diabetes Prediction and Prevention (DIPP) study. The samples covered the time span from before the development of autoantibodies (seroconversion) through the diagnosis of diabetes. Healthy, persistently autoantibody-negative children matched for date and place of birth, gender and the HLA-DQB1-conferred genetic risk were chosen as controls. Children who eventually developed T1D are herein sometimes referred to as "cases".

Quantitative analyses of the data resulted in identification of proteins that may be used to predict T1D risk and provide indications of disease onset prior to diagnosis and, surprisingly, even prior to seroconversion. The identified predictive protein marker panels may be grouped into three different categories on the basis of their temporal utility in predicting T1D risk.

Figure 6:
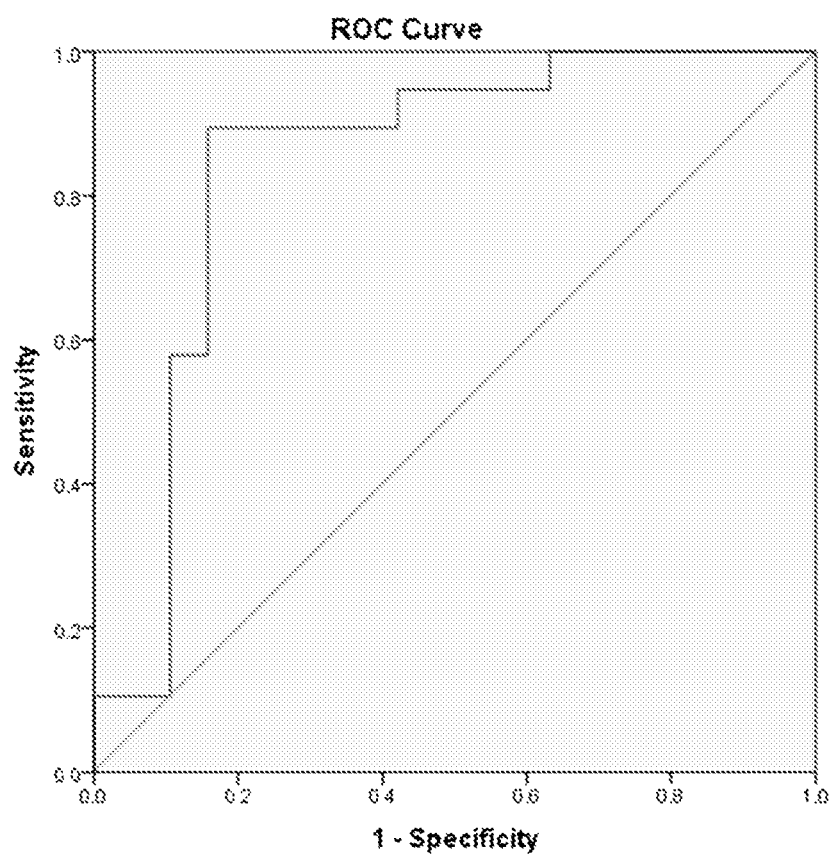
FIG. 6 illustrates the receiver-operator characteristic (ROC) curve of the abundance of PROF1 and FLNA as detected three to six months prior to autoantibody seroconversion.

A first identified temporal category of protein markers is based on changes in protein abundance prior to seroconversion, particularly 3 to 6 months prior to seroconversion. The expression of these proteins either increases or decreases before seroconversion. As is described in the Examples below, analyses of the receiver operator characteristics of the data provided good classification of the children en route to T1D with respect to their controls. To be more specific, in samples collected within a 6 months' time period prior to seroconversion, increased levels of PROF1 were observed with a consistency sufficient for observing an AUC of 0.85 in the ROC analysis. Further analysis revealed that the combination of PROF1 and FLNA provided an AUC of 0.88 (FIG. 6).

Thus, in an embodiment of the present invention, T1D risk prediction, preferably prior to seroconversion, is based on determining the protein marker profile of PROF1 and FLNA, and comparing the determined protein marker profile with that of a control. Increased expression of the protein marker profile with respect to the control marker profile is indicative of a risk of getting T1D.

Figure 7:
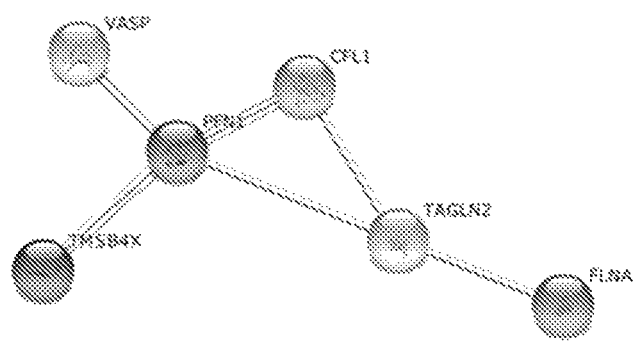
FIG. 7 illustrates the outcome of pathway analysis of differentially abundant proteins three to six months prior to autoantibody seroconversion, emphasizing the putative importance of these proteins in events preceding seroconversion. The abbreviations used in the figure refer to genes encoding the listed proteins.

Pathway analysis of differentially abundant proteins three to six months prior to autoantibody seroconversion revealed biochemical associations between PROF1, FLNA, TAGL2, VASP, CFL1, ACTB, and TMSB4X (FIG. 7). Thus, PROF1 and FLNA based classification of at-risk subjects and unaffected subjects may be improved by including any one of proteins markers TAGL2, VASP, CFL1, ACTB, and TMSB4X, either alone or in any combination, in the protein marker profile to be determined for predicting the risk of T1D.

A second identified temporal category of protein markers is based on changes in protein abundance, as compared to control levels, throughout the time series. In other words, these markers may be used for predicting the risk of T1D either before or after seroconversion. The expression of these proteins is either increased or decreased across the time series.

Figure 8A:
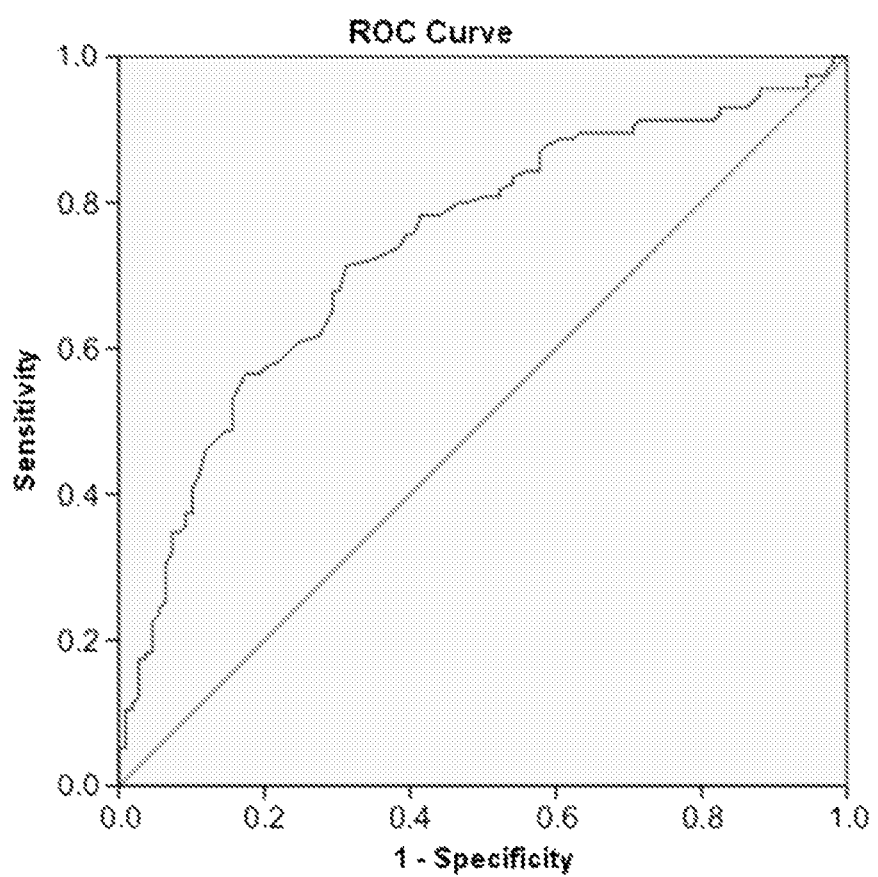
Figure 8B:
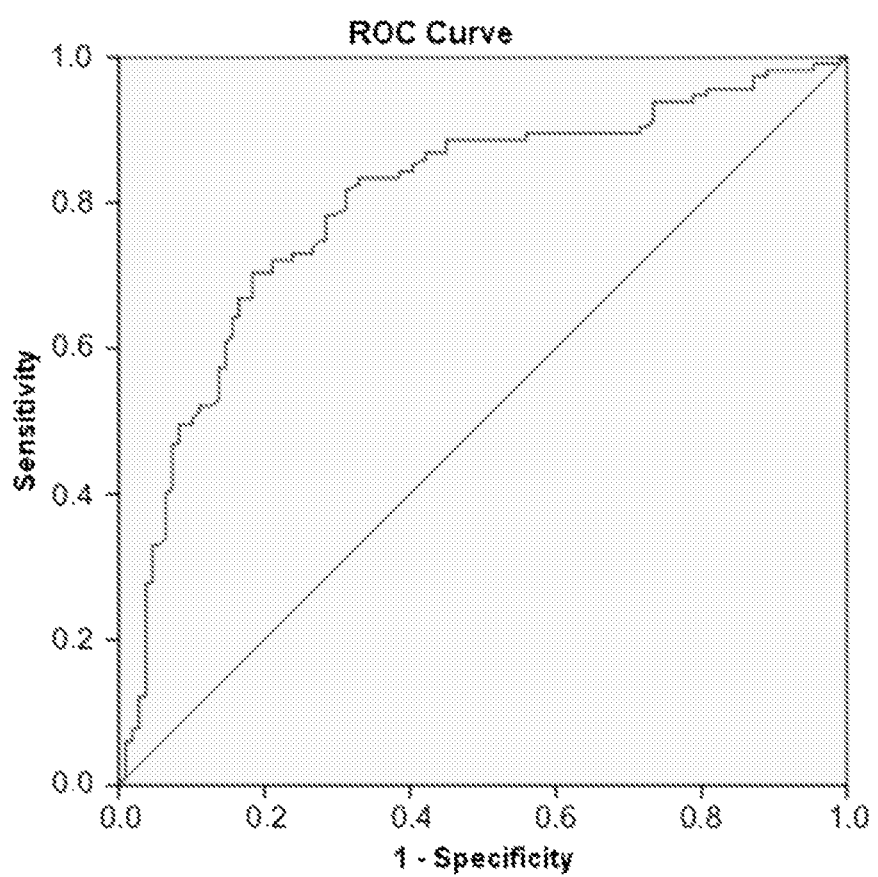
FIG. 8B illustrates SHBG vs. CO8G, ZPI, BTD, CO5, and THBG (AUC=0.80).

A first protein marker panel belonging to the second temporal category comprises SHBG either alone or in any combination with one or more of protein markers CO8G, ZPI, BTD, CO5, and THBG. According to the present results, the expression of SHBG was decreased while the expression of CO8G, ZPI, BTD, CO5, and THBG was increased in the T1D-developing children as compared with the expression levels in the control samples. On its own, SHBG gave an AUC of 0.74 but when used in combination with any one of CO8G, ZPI, BTD, CO5, and THBG, the AUC was improved to the order of 0.8 (FIGS. 8A and 8B).

Thus, in an embodiment of the present invention, T1D risk prediction is based on determining the protein marker profile of SHBG either alone in any combination with one or more of protein markers selected from the group consisting of CO8G, ZPI, BTD, CO5, and THBG, and comparing the determined protein marker profile with that of a control. Differences in the protein marker profile with respect to the control marker profile are indicative of a risk of developing T1D. These marker profiles are suitable for being utilized either in a time period prior to seroconversion or from the seroconverted state to diagnosis.

Figures 4A, 4B:
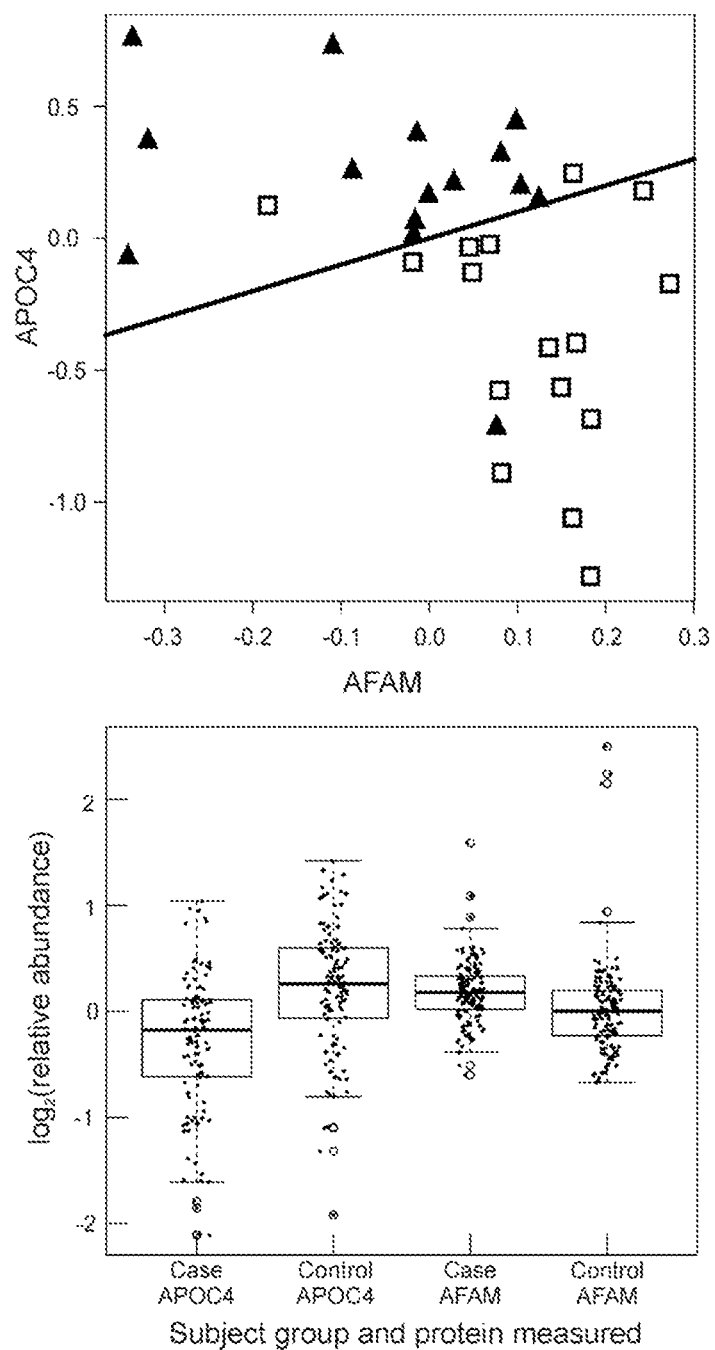
FIG. 4A shows classification between T1D-developing subjects and age-matched controls on the basis of the abundance of APOC4 and AFAM. The top scoring pairs method was used, yielding a 91% success rate. Black triangles represent the controls and open squares represent the T1 D-developing children (i.e. cases).
FIG. 4B illustrates relative abundance measurements for APOC4 and AFAM for the case and control subjects.
Figure 5A:
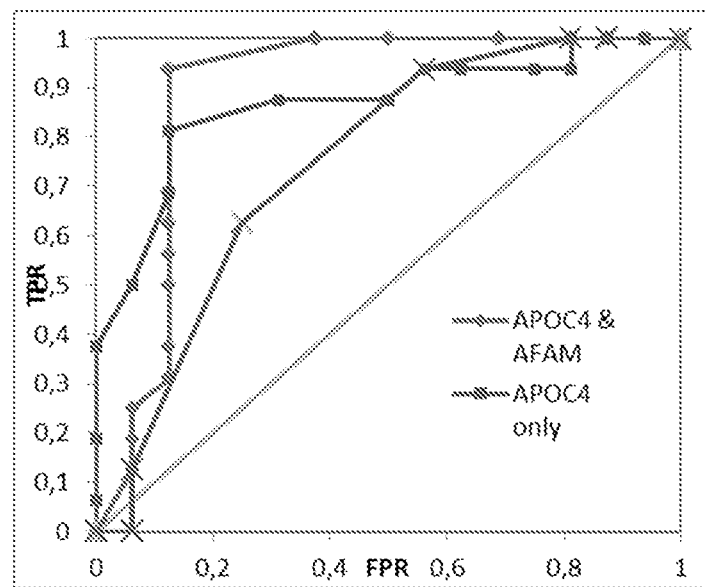
FIG. 5A illustrates receiver-operator characteristics on the basis of the differences between APOC4 and AFAM levels and the individual effect of these proteins alone. The combination of APOC4 and AFAM gave an area under the curve (AUC) of 0.89.
Figure 5B:
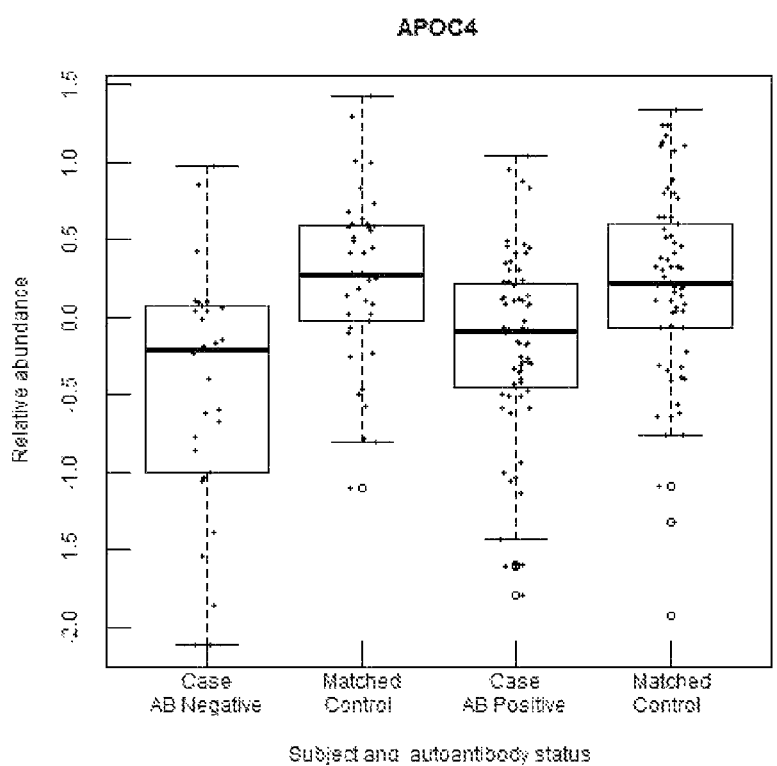
FIG. 5B illustrates APOC4 levels in cases and controls, before seroconversion and in antibody positive subjects vs. age matched controls.

A second protein marker panel belonging to the second temporal category comprises APOC4 and AFAM. As is described in the Examples below, statistical analysis of clinical samples revealed that APOC4 and AFAM, preferably in combination, are protein markers remarkably effective in determining the risk of T1D with clinically acceptable detection and false positive rates. Herein, APOC4 and AFAM were consistently detected at disparate levels, lower and higher, respectively, in prospective samples of children who developed T1D. Taken together, a success rate of 91% with a false positive rate of 5% on the basis of APOC4 together with AFAM levels was determined (FIG. 4A). The ROC analysis of APOC4 in combination with AFAM gave an AUC of 0.87 (FIG. 5A).

Thus, in an embodiment of the present invention, T1D risk prediction is based on determining the protein marker profile of APOC4 and AFAM, and comparing the determined protein marker profile with that of a control. Differences in the protein marker profile with respect to the control marker profile are indicative of a risk of developing T1D.

Figure 9:
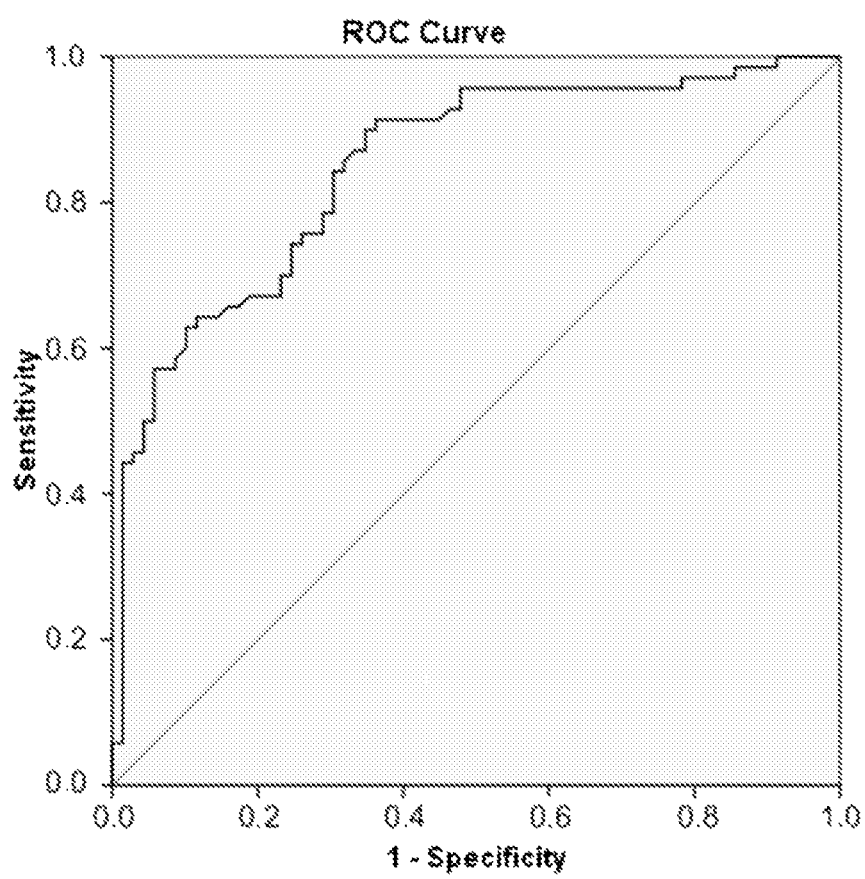
FIG. 9 illustrates the receiver-operator characteristic (ROC) curve of the abundance of SHBG vs IBP2, ADIPO, CO2, and CO8G (AUC=0.85) post seroconversion.

A third identified temporal protein marker panel comprises proteins whose expression levels reflect the transition of the seroconverted state towards diagnosis. The present data analyses revealed that progression to T1D is characterized by decreasing IBP2 and ADIPO, and increasing CO2. Thus, seroconverted patients should be monitored for these protein markers as indicators of pre-disease severity and/or to identify any need for intervention, moreover, when taken together with the contrast provided together with SHBG and CO8G (FIG. 9).

Thus, in an embodiment of the present invention, T1D risk prediction is based on determining the protein marker profile of IBP2, ADIPO, and CO2, and comparing the determined protein marker profile with that of a control. Differences in the protein marker profile with respect to the control marker profile are indicative of a risk of developing T1 D. In a further embodiment, said marker profile includes, in addition to IBP2, ADIPO, and CO2, either one or both of SHBG and CO8G.

In some embodiments, the above-defined protein marker panels may be used in any desired combination. Thus, a protein marker panel comprising PROF1 and FLNA and, optionally, at least one of TAGL2, VASP, CFL1, ACTB, and TMSB4X, may be used in combination with a protein marker panel comprising SHBG and, optionally at least one of CO8G, ZPI, BTD, CO5, and THBG, or with a protein marker panel comprising APOC4 and AFAM, or with a protein marker panel comprising IBP2, ADIPO, and CO2 and, optionally, one or both of SHBG and CO8G. Likewise, in some embodiments, a protein marker panel comprising SHBG and, optionally at least one of CO8G, ZPI, BTD, CO5, and THBG, may be used in combination with a protein marker panel comprising APOC4 and AFAM, or with a protein marker panel comprising IBP2, ADIPO, and CO2, and optionally one or both of SHBG and CO8G. Likewise, a protein marker profile comprising APOC4 and AFAM may be used in combination with a protein marker panel comprising IBP2, ADIPO, and CO2, and optionally one or both of SHBG and CO8G.

In some embodiments, assessing or predicting an individual's risk for T1D may be based on determining, in addition to the protein marker profiles set forth above, the level or amount of one or more protein markers set forth in Table 4 and/or Table 5 The selection of one or more of these additional protein markers to be used may depend on a variety of practical considerations such as availability of protein marker testing reagents or equipment.

In summary, using mass spectrometry based analysis of immuno-depleted sera, the present inventors have demonstrated for the first time serum proteomics profiles of the pre-diabetic transition all the way to the diagnosis, comparing profiles between children progressing to type 1 diabetes and healthy children. These results demonstrate shared and group specific longitudinal changes against a back-ground of wide subject heterogeneity, suggesting that components of the moderately abundant serum proteins may be indicative of the emerging threat of type 1 diabetes.

Optionally, the present methods may further comprise determining variations in the individual's proteomic profile at different time points in order to monitor, preferably prior to seroconversion, any changes in the development of the risk for T1D.

In some implementations, the present methods of predicting an individual's risk for T1 D may further include therapeutic intervention. Once an individual is identified to have an increased risk for T1D, he/she may be subjected to, for instance, dietary or other changes in the individual's lifestyle.

In some further implementations, the herein identified panels of predictive protein markers may be used for screening new therapeutics or preventive drugs for T1D. In other words, the present panels may be used for assessing whether or not a candidate drug is able to correct the protein marker profile of an at-risk individual towards that of an unaffected individual. For example, individuals identified to have an increased risk for T1D on the basis of their protein marker profile belonging to either the first or second temporal category of predictive protein markers could be employed as targets in preventive vaccination trials or in trials aimed for identifying preventive agents, such as probiotics, for T1D.

In some still further embodiments and implementations, the herein identified panels of protein markers may be used for determining an individual's stage of progression towards T1D and/or for monitoring or predicting an individual's progression towards T1D. Said stage of progression may be a pre-seroconversion stage, e.g. 3 to 6 months pre-seroconversion or 9 to 12 months pre-seroconversion, or a post-seroconversion stage, e.g. 3 to 6 months pre-diagnosis, 9 to 12 months pre-diagnosis, or 15 to 18 months pre-diagnosis. Of the herein disclosed panels of protein markers, panel i), i.e. PROF1 and FLNA, optionally, with one or more protein markers selected from the group consisting of TAGL2, VASP, CFL1, ACTB, and TMSB4X, is particularly suitable for monitoring said individual's T1D progression at the pre-seroconversion stage and predicting progression to the post-seroconversion stage, e.g. such that said individual is predicted to face the post-seroconversion stage e.g. within 9 to 12 months or 3 to 6 months. The protein marker panel ii), i.e. SHBG, optionally, with one or more protein markers selected from the group consisting of CO8G, ZPI, BTD, CO5, and THBG, and/or the protein marker panel iii), i.e. AFAM and APOC4, may also be used as set forth above regarding the panel i) but, alternatively or in addition, they may also be used for monitoring said individual's T1D progression at the post-seroconversion stage or predicting progression to T1D diagnosis, e.g. such that said individual is predicted to face the T1D diagnosis e.g. within 9 to 12 months or 3 to 6 months. The panel iv), i.e. IBP2, ADIPO, and CO2, optionally, with one or both of SHBG and CO8G, is particularly suitable for monitoring said individual's T1D progression at the post-seroconversion stage or predicting progression to T1D diagnosis, e.g. such that said individual is predicted to face the T1D diagnosis e.g. within 9 to 12 months or 3 to 6 months.

In some still further implementations, the present disclosure relates to an in vitro kit for predicting, preferably before seroconversion, a risk of a subject for developing T1D. The kit may be used in any one of the methods of the present disclosure. Typically, the kit comprises one or more testing agents for testing a sample obtained from an individual whose risk for T1D is to be determined for any one or more of the protein marker panels disclosed herein indicative of a risk of developing T1 D. In some embodiments, the kit may comprise one or more testing agents which recognize a protein marker profile comprising:

i) PROF1 and FLNA, and, optionally, also one or more protein markers selected from the group consisting of TAGL2, VASP, CFL1, ACTB, and TMSB4X;

ii) SHBG and, optionally, also one or more protein markers selected from the group consisting of CO8G, ZPI, BTD, CO5, and THBG;

iii) AFAM and APOC4; or iv) IBP2, ADIPO, and CO2 and, optionally, one or both of SHBG and CO8G.

In some embodiments, the kit may also comprise testing agents for any protein marker, or a combination thereof, listed in Table 4 or 5.

The kit may also comprise a computer readable medium comprising computer-executable instructions for performing any method of the present disclosure.

It will be obvious to a person skilled in the art that, as technology advances, the inventive concept can be implemented in various ways. The invention and its embodiments are not limited to the examples described below but may vary within the scope of the claims.

EXAMPLES

Example 1. Research Design and Methods

A schematic of the experimental design used in the identification of these markers is illustrated in FIG. 1. Detailed description of the proteomic measurements, samples and comparisons are provided in Example 2.

Subjects and Sample Collection

All children studied were participants in the Finnish DIPP study, where children identified as at risk for type 1 diabetes based on their HLA genotype were followed prospectively from birth. Venous non-fasting blood samples were collected from the children at each study visit. Sera were separated and stored at −70° C. within three hours from the blood sample collections. Serum islet cell autoantibodies (ICA) measurements were made as previously described. For ICA positive children, glutamic acid decarboxylase (GADA), tyrosine phosphatase-related protein antibodies (IA-2A), and insulin antibodies (IAA) were also determined.

Figure 2:
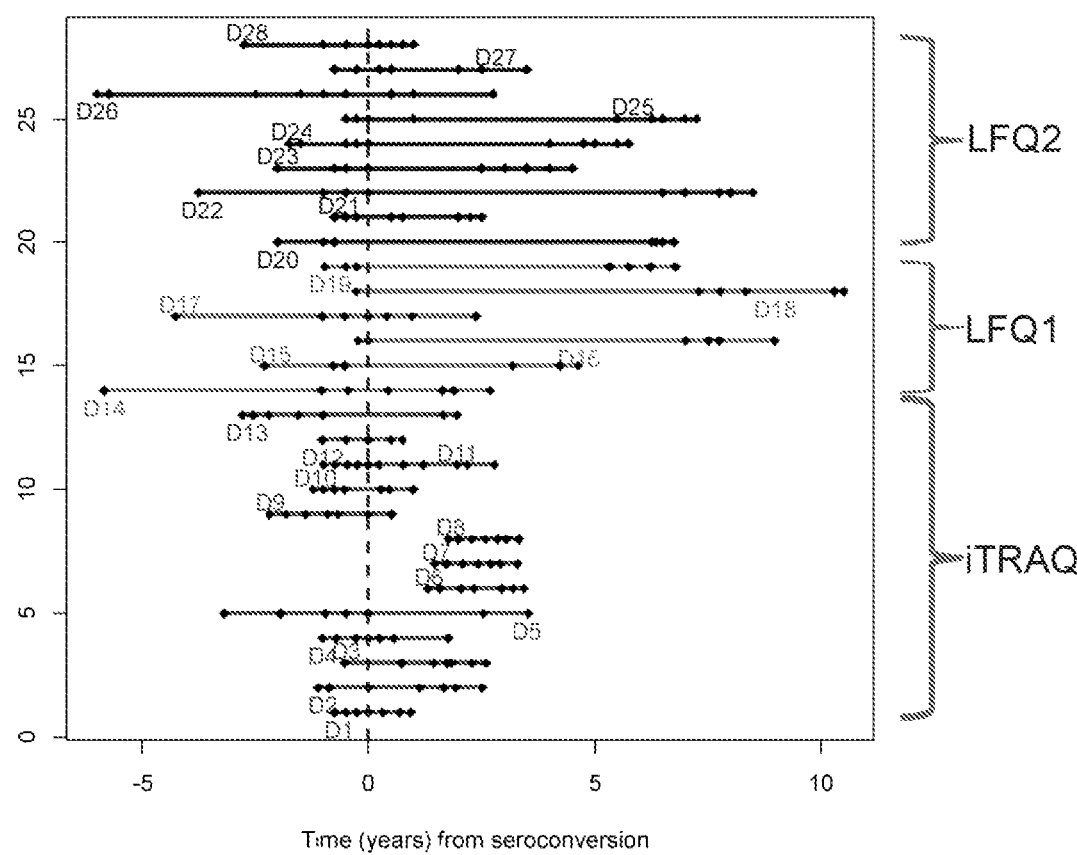
FIG. 2 shows timing of the serum samples used, represented relative to the first detection of T1D-associated autoantibodies in years. The samples profiled for the T1D-developing children are represented by black diamonds. These include iTRAQ measurements (13 pairs) and label free measurements in two batches (LFQ1 and LFQ2, n=6 and 9 pairs respectively). For the comparison between children (healthy vs. type 1 diabetes developing) the analyses considered protein abundance throughout the series (184 vs. 184 age-matched samples), samples before (71 vs. 71 age-matched samples), and after detection of seroconversion (113 vs. 113 age-matched samples).

Proteomic measurements were made on sera from 28 case children who developed type 1 diabetes during DIPP follow-up. Prospective serum samples (5-11 per child) were selected to represent different phases of T1D progression from autoantibody-negativity to seroconversion (SC) and further until the overt disease. A persistently autoantibody negative control child was matched with each case (typically in the order of seven samples per child), based on the date and place of birth, gender and HLA-DQB1 genotype. The prospective control serum samples were matched with the case samples by age at sample draw. Altogether 409 serum samples were analyzed, of which sera from twenty-six children (13 case-control pairs) were processed for iTRAQ analysis, and from thirty children (15 case-control pairs) for analysis using a label free approach (Table 2, FIG. 2).

TABLE 2

Summary of the children progressing to T1D whose samples were studied with proteomics

| ID | Gender | HLA-DQB1 risk alleles | Age at seroconversion (years) | Age at diagnosis (years) | Number of samples analyzed (case and control) | Analysis Method |
|---|---|---|---|---|---|---|
| D1 | M | *02, *03:02 | 1.3 | 2.2 | 7 & 7 | iTRAQ |
| D2 | M | *02, *03:02 | 1.4 | 4.0 | 7 & 7 | iTRAQ |
| D3 | M | *02, *03:02 | 1.3 | 3.9 | 7 & 7 | iTRAQ |
| D4 | F | *02, *03:02 | 1.5 | 3.3 | 7 & 7 | iTRAQ |
| D5 | F | *02, *03:02 | 3.4 | 7.0 | 7 & 7 | iTRAQ |
| D6 | F | *02, *03:02 | 0.5 | 4.0 | 7 & 7 | iTRAQ |
| D7 | F | *02, *03:02 | 0.6 | 4.1 | 7 & 7 | iTRAQ |
| D8 | M | *02, *03:02 | 1.0 | 4.4 | 7 & 7 | iTRAQ |
| D9 | M | *02, *03:02 | 2.5 | 3.6 | 7 & 7 | iTRAQ |
| D10 | M | *03:02, x | 1.5 | 2.5 | 7 & 7 | iTRAQ |
| D11 | M | *03:02, x | 1.3 | 4.0 | 11 & 9 | iTRAQ |
| D12 | M | *03:02, x | 2.0 | 2.2 | 5 & 7 | iTRAQ |
| D13 | M | *03:02, x | 3.5 | 5.5 | 7 & 6 | iTRAQ |
| D14 | M | *02, *03:02 | 6.1 | 8.8 | 7 & 8 | LFQ |
| D15 | M | *02, *03:02 | 2.6 | 8.3 | 6 & 7 | LFQ |
| D16 | F | *02, *03:02 | 1.0 | 10.0 | 6 & 6 | LFQ |
| D17 | F | *02, *03:02 | 5.0 | 7.7 | 7 & 7 | LFQ |
| D18 | M | *03:02, x | 1.3 | 12.1 | 6 & 8 | LFQ |
| D19 | F | *03:02, x | 1.3 | 8.6 | 7 & 8 | LFQ |
| D20 | M | *03:02, x | 2.5 | 6.6 | 9 vs. 9 | LFQ |
| D21 | M | *02, *03:02 | 4.0 | 12.5 | 9 vs. 8 | LFQ |
| D22 | F | *02, *03:02 | 2.0 | 7.8 | 9 vs. 8 | LFQ |
| D23 | F | *02, *03:02 | 1.0 | 3.6 | 7 vs 7 | LFQ |
| D24 | F | *02, *03:02 | 1.4 | 8.6 | 8 vs 9 | LFQ |
| D25 | F | *02, *03:02 | 6.5 | 9.3 | 9 vs 8 | LFQ |
| D26 | F | *02, *03:02 | 2.2 | 9.2 | 7 vs. 7 | LFQ |
| D27 | M | *03:02, x | 3.0 | 4.3 | 8 vs 6 | LFQ |
| D28 | M | *02, *03:02 | 1.3 | 3.8 | 8 vs 8 | LFQ | x ≠ *02, *03:01, *06:02/3

See also Tables 3a b & c in Example 2 for more information on the cases and their matched controls.

Sample Preparation

Serum samples were depleted of the most abundant proteins using immuno-affinity columns. Beckman-Coulter (IgY-12) and Agilent (Hu14) columns were used in this study, where the same depletion method was always applied to follow-up samples of each case-control pair.

Figure 3:
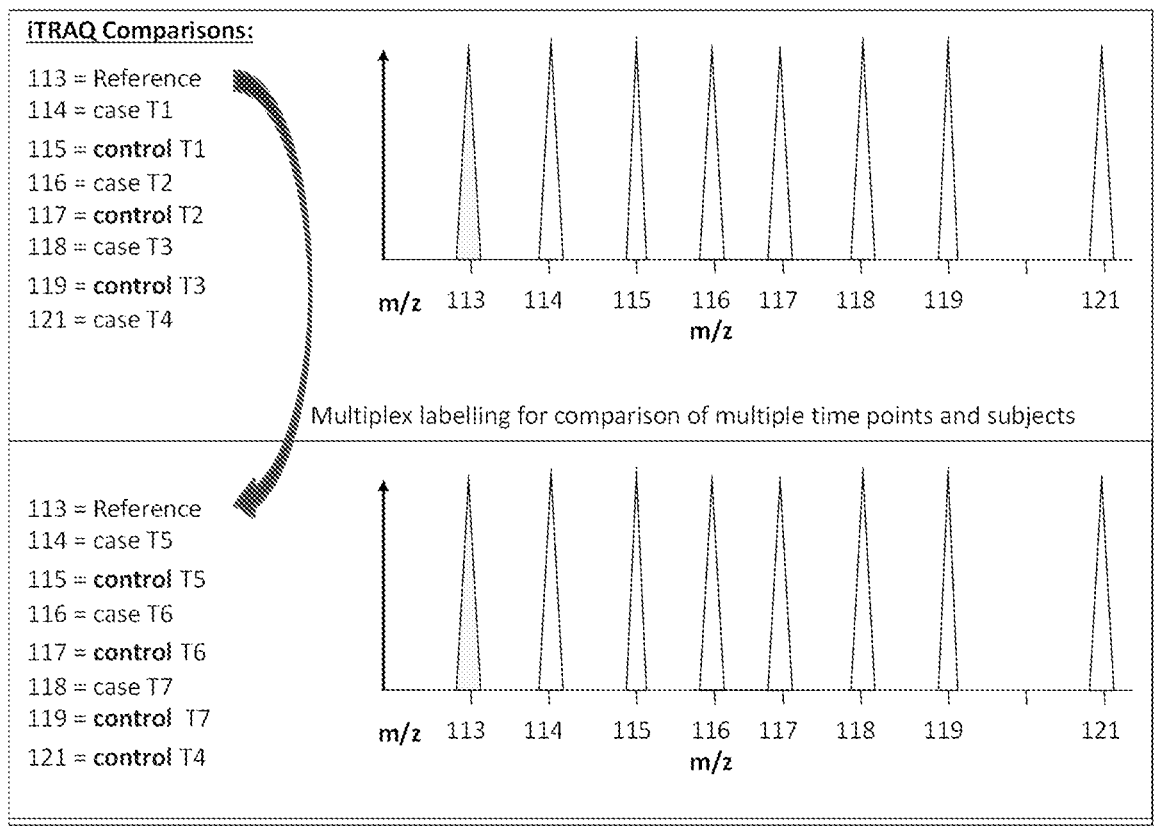
FIG. 3 is a schematic representation of the 8-plex iTRAQ labelling strategy. Pool reference channels were used to link iTRAQ comparisons between experiments.

Samples from twenty-six children were compared using the iTRAQ method, using twenty-seven paired/cross referenced 8-plex ITRAQ labelling schemes of the samples. For iTRAQ labelling, the samples were then processed in accordance with the manufacturer's protocol for 8-plex reagents (ABSciex, Framingham, Mass., USA), then fractionated using strong cation exchange chromatography. The typical labelling scheme for the iTRAQ measurements was as indicated in FIG. 3, where a pooled reference was used to link experiments.

Samples from thirty children were compared using label free quantification (LFQ), with concentration and digestion performed in a similar manner as the iTRAQ samples, with the digests otherwise unfractionated prior to LC-MS/MS. Two batches of analysis were made, namely LFQ1 (n=6 pairs) and LFQ2 (n=9 pairs).

LC-MS/MS Analysis

HPLC-tandem mass spectral analyses (LC-MS/MS) were made with a QSTAR-Elite time of flight instrument (TOF) and an Orbitrap-Velos Fourier transform (FT) instrument. For the analysis of iTRAQ labelled samples, the collision induced dissociation and higher-energy collisional dissociation modes were used to record positive ion tandem mass spectra for the QSTAR-Elite and Orbitrap-Velos, respectively. The label-free data were acquired with the Orbitrap-Velos using collision induced dissociation. Chromatographic separations were made with 150 mm×75 μm i.d. tapered columns packed with Magic C18-bonded silica (200A), using binary gradients of water and acetonitrile with 0.2% formic acid.

LC-MS/MS Data Processing

The iTRAQ data were analyzed using ProteinPilot™ software using the Paragon™ identification algorithm with a Human Swiss-Prot database (Aug. 18, 2011, 20245 entries). The database searches were made in thorough mode specifying 8-plex-iTRAQ quantification, trypsin digestion and MMTS modification of cysteine. ITRAQ ratios were calculated relative to the reference samples using Protein-Pilot™.

The label-free data were analyzed with Proteome Discover version 1.3 (Thermo Scientific) together with Mascot (2.1, Matrix Science). The database search criteria were trypsin digestion, MMTS modification of cysteine, deamidation of N/Q and methionine oxidation, using the same database. The mass tolerance settings of 5 ppm for the precursors and 0.5 Da for fragments were used. For quantitative analysis, Pro-genesis software (version 4.0) was used for feature detection and alignment of the ion maps and calculation of intensity-based abundance measurements for each protein. To facilitate comparison of the label free data with the iTRAQ results, the intensity values of each protein was scaled relative to the median intensity of each protein across the paired case-control sample series.

Data Analysis

Serum proteomics differences between healthy children and those progressing to type 1 diabetes. Case-control abundance ratios were calculated for the paired samples. The ratios were $\log_2$ transformed and used in rank product analysis (RP) as is well known in the art to identify differences either throughout the time series (n=28), prior to the detection of autoantibody seroconversion (n=23) and prior to diagnosis (n=28). The RP analyses were made with 10,000 times permutations, and a false discovery rate (FDR) of less than or equal to 5% was applied (Benjamini-Hochberg (BH) correction). The differences analyzed were made for the average case-control ratios at the following time intervals (selected on the basis of the similarity of the sample series used): throughout the time series; prior to seroconversion, i.e. 3 to 6 months, 9 to 12 months and the overall period; prior to diagnosis, i.e. 3 to 6 months, 9 to 12 months, within 1.5 years and overall. Additional statistical tests were made using the Wilcoxon Rank-sum test.

Serum proteomics changes in children progressing to type 1 diabetes. Spearman's rank correlation analyses were made to assess whether any of the protein profiles were correlated with the emergence of T1D. The analyses were made for the collected case—control abundance ratios of the paired samples. For this comparison there were eleven well matched pairs with samples before and after seroconversion (subjects D1, D4, D5, D9, D10, D11, D12, D14, D15, D17, D19). The analysis was repeated separately for the case and control subjects to reference ratios. To unify this analysis the age/time axis was scaled between birth and diagnosis (zero to one). A Spearman's correlation coefficient greater than 0.4 was considered as a valid weak correlation (p-value based on 10,000 permutations of the time axis. BH corrected FDR≤0.05).

Subject and status classification. The top scoring pairs (TSP) method was applied to identify whether combinations of the quantified proteins could classify the samples and subjects. The leave-one-out method was used for cross validation. The method was tested in terms of relative protein abundance throughout the time series, before or after seroconversion, as well as for the intra individual longitudinal changes putatively associated with seroconverted status. The within subject averaged $\log_2$ protein relative abundance values were used for the time periods studied. In the preliminary data (ITRAQ and LFQ1) APOC4 was detected in 16 out of 19 subject pairs, the 16 were separately analyzed with the TSP method. The failure to quantify APOC4 in all children was attributed to differences in instrument performance rather than its absence.

Example 2. Supplemental Information on Samples

Subjects and Samples

Details of serum samples obtained children progressing to type 1 diabetes (D) and their matched controls (C) are shown in Tables 3a, 3b, and 3c below.

TABLE 3a

| iTRAQ samples | | | | | | | | | | |
|---|---|---|---|---|---|---|---|---|---|---|
| Case Sample name | Gender | HLA-DQB1 risk alleles | Age at sample | Time from SC | Time from T1D diagnosis | Ab+ve | Control Sample name | Gender | HLA-DQB1 risk alleles | Age at sample/ days |
| D1_1 | Male | 02/ | 193 | −274 | 683 | 0 | C1_1 | Male | 02/ | 193 |
| D1_2 | | 0302 | 284 | −183 | 592 | 0 | C1_2 | | 302 | 288 |
| D1_3 | | | 375 | −92 | 501 | 0 | C1_3 | | | 367 |
| D1_4 | | | 467 | 0 | 409 | 1 | C1_4 | | | 465 |
| D1_5 | | | 584 | 117 | 292 | 1 | C1_5 | | | 557 |
| D1_6 | | | 719 | 252 | 157 | 1 | C1_6 | | | 743 |
| D1_7 | | | 807 | 340 | 69 | 1 | C1_7 | | | 932 |
| D2_1 | Male | 02/ | 122 | −407 | −1396 | 0 | C2_1 | Male | 02/ | 279 |
| D2_2 | | 0302 | 529 | 0 | −989 | 1 | C2_2 | | 302 | 455 |
| D2_3 | | | 724 | 195 | −794 | 1 | C2_3 | | | 552 |
| D2_4 | | | 940 | 411 | −578 | 1 | C2_4 | | | 742 |
| D2_5 | | | 1143 | 614 | −375 | 1 | C2_5 | | | 914 |
| D2_6 | | | 1234 | 705 | −284 | 1 | C2_6 | | | 1107 |
| D2_7 | | | 1446 | 917 | −72 | 1 | C2_7 | | | 1470 |
| D3_1 | Male | 02/ | 278 | −195 | −1145 | 0 | C3_1 | Male | 2/ | 278 |
| D3_2 | | 0302 | 740 | 267 | −683 | 0 | C3_2 | | 302 | 559 |
| D3_3 | | | 1004 | 531 | −419 | 1 | C3_3 | | | 636 |
| D3_4 | | | 1110 | 637 | −313 | 1 | C3_4 | | | 722 |
| D3_5 | | | 1146 | 673 | −277 | 1 | C3_5 | | | 925 |
| D3_6 | | | 1308 | 835 | −115 | 1 | C3_6 | | | 1092 |
| D3_7 | | | 1423 | 950 | 0 | 1 | C3_7 | | | 1286 |
| D4_1 | Female | 02/ | 183 | −370 | −1016 | 0 | C4_1 | Female | 02/ | 190 |
| D4_2 | | 0302 | 299 | −254 | −900 | 0 | C4_2 | | 302 | 370 |
| D4_3 | | | 453 | −100 | −746 | 0 | C4_3 | | | 453 |
| D4_4 | | | 553 | 0 | −646 | 0 | C4_4 | | | 547 |
| D4_5 | | | 645 | 92 | −554 | 1 | C4_5 | | | 644 |
| D4_6 | | | 756 | 203 | −443 | 1 | C4_6 | | | 730 |
| D4_7 | | | 1199 | 646 | 0 | 1 | C4_7 | | | 1192 |
| D5_1 | Female | 201/ | 87 | −1169 | −2462 | 0 | C5_1 | Female | 201/ | 92 |
| D5_2 | | 0302 | 547 | −709 | −2002 | 0 | C5_2 | | 302 | 567 |

TABLE 3a-continued

| iTRAQ samples | | | | | | | | | |
|---|---|---|---|---|---|---|---|---|---|
| Case Sample name | Gender | HLA-DQB1 risk alleles | Age at sample | Time from SC | Time from T1D diagnosis | Ab + ve | Control Sample name | Gender | HLA-DQB1 risk alleles | Age at sample/ days |
| D5_3 | | | 907 | −349 | −1642 | 0 | C5_3 | | | 902 |
| D5_4 | | | 1073 | −183 | −1476 | 0 | C5_4 | | | 1092 |
| D5_5 | | | 1256 | 0 | −1293 | 0 | C5_5 | | | 1296 |
| D5_6 | | | 2187 | 931 | −362 | 1 | C5_6 | | | 2184 |
| D5_7 | | | 2549 | 1293 | 0 | 1 | C5_7 | | | 2571 |
| D6_1 | Male | 201/ | 673 | 479 | −899 | 1 | C6_1 | Male | 201/ | 549 |
| D6_2 | | 0302 | 769 | 575 | −803 | 1 | C6_2 | | 302 | 637 |
| D6_3 | | | 944 | 750 | −628 | 1 | C6_3 | | | 727 |
| D6_4 | | | 1047 | 853 | −525 | 1 | C6_4 | | | 913 |
| D6_5 | | | 1271 | 1077 | −301 | 1 | C6_5 | | | 1090 |
| D6_6 | | | 1364 | 1170 | −208 | 1 | C6_6 | | | 1273 |
| D6_7 | | | 1450 | 1256 | −122 | 1 | C6_7 | | | 1452 |
| D7_1 | Female | 201/ | 733 | 532 | −753 | 1 | C7_1 | Female | 201/ | 659 |
| D7_2 | | 0302 | 833 | 632 | −653 | 1 | C7_2 | | 302 | 735 |
| D7_3 | | | 964 | 763 | −522 | 1 | C7_3 | | | 910 |
| D7_4 | | | 1087 | 886 | −399 | 1 | C7_4 | | | 1099 |
| D7_5 | | | 1188 | 987 | −298 | 1 | C7_5 | | | 1275 |
| D7_6 | | | 1265 | 1064 | −221 | 1 | C7_6 | | | 1464 |
| D7_7 | | | 1402 | 1201 | −84 | 1 | C7_7 | | | 1653 |
| D8_1 | Male | 201/ | 1018 | 646 | −643 | 1 | C8_1 | Male | 201/ | 640 |
| D8_2 | | 0302 | 1102 | 730 | −559 | 1 | C8_2 | | 302 | 730 |
| D8_3 | | | 1207 | 835 | −454 | 1 | C8_3 | | | 900 |
| D8_4 | | | 1318 | 946 | −343 | 1 | C8_4 | | | 1101 |
| D8_5 | | | 1410 | 1038 | −251 | 1 | C8_5 | | | 1255 |
| D8_6 | | | 1486 | 1114 | −175 | 1 | C8_6 | | | 1465 |
| D8_7 | | | 1590 | 1218 | −71 | 1 | C8_7 | | | 1640 |
| D9_1 | Male | 201/ | 102 | −795 | −1206 | 0 | C9_1 | Male | 201/ | 103 |
| D9_2 | | 0302 | 233 | −664 | −1075 | 0 | C9_2 | | 302 | 273 |
| D9_3 | | | 392 | −505 | −916 | 0 | C9_3 | | | 366 |
| D9_4 | | | 567 | −330 | −741 | 0 | C9_4 | | | 525 |
| D9_5 | | | 654 | −243 | −654 | 0 | C9_5 | | | 614 |
| D9_6 | | | 897 | 0 | −411 | 0 | C9_6 | | | 923 |
| D9_7 | | | 1086 | 189 | −222 | 1 | C9_7 | | | 1100 |
| D10_1 | Male | 302 | 118 | −446 | −882 | 0 | C10_1 | Male | 302 | 109 |
| D10_2 | | | 201 | −363 | −799 | 0 | C10_2 | | | 204 |
| D10_3 | | | 280 | −284 | −720 | 0 | C10_3 | | | 293 |
| D10_4 | | | 371 | −193 | −629 | 0 | C10_4 | | | 397 |
| D10_5 | | | 663 | 99 | −337 | 1 | C10_5 | | | 670 |
| D10_6 | | | 731 | 167 | −269 | 1 | C10_6 | | | 733 |
| D10_7 | | | 927 | 363 | −73 | 1 | C10_7 | | | 922 |
| D11_1 | Male | 302 | 98 | −363 | −1372 | 0 | C11_1 | Male | 302 | 89 |
| D11_2 | | | 188 | −273 | −1282 | 0 | C11_2 | | | 208 |
| D11_3 | | | 289 | −172 | −1181 | 0 | C11_3 | | | 292 |
| D11_4 | | | 370 | −91 | −1100 | 0 | C11_4 | | | 360 |
| D11_5 | | | 461 | 0 | −1009 | 0 | C11_5 | | | 454 |
| D11_6 | | | 548 | 87 | −922 | 0 | C11_6 | | | 542 |
| D11_7 | | | 743 | 282 | −727 | 0 | C11_7 | | | 738 |
| D11_8 | | | 902 | 441 | −568 | 0 | C11_8 | | | 929 |
| D11_9 | | | 1179 | 718 | −291 | 1 | C11_9 | | | 1272 |
| D11_10 | | | 1261 | 800 | −209 | 1 | C11_10 | | | 1456 |
| D11_11 | | | 1476 | 1015 | 6 | 1 | | | | |
| D12_1 | Male | 302 | 160 | −553 | −731 | 0 | C12_1 | Male | 302 | 132 |
| D12_2 | | | 349 | −364 | −542 | 0 | C12_2 | | | 302 |
| D12_3 | | | 531 | −182 | −360 | 0 | C12_3 | | | 386 |
| D12_4 | | | 713 | 0 | −178 | 1 | C12_4 | | | 473 |
| D12_5 | | | 807 | 94 | −84 | 1 | C12_5 | | | 665 |
| | | | | | | | C12_6 | | | 739 |
| | | | | | | | C12_7 | | | 903 |
| D13_1 | Female | 302 | 271 | −1022 | −1739 | 0 | C13_1 | Female | 302 | 293 |
| D13_2 | | | 363 | −930 | −1647 | 0 | C13_2 | | | 398 |
| D13_3 | | | 488 | −805 | −1522 | 0 | C13_3 | | | 494 |
| D13_4 | | | 729 | −564 | −1281 | 0 | C13_4 | | | 721 |
| D13_5 | | | 917 | −376 | −1093 | 0 | C13_5 | | | 910 |
| D13_6 | | | 1897 | 604 | −113 | 1 | C13_6 | | | 1834 |
| D13_7 | | | 2009 | 716 | −1 | 1 | | | | |

TABLE 3b

Label-free samples LFQ1

| Case Sample name | Gender | HLA-DQB1 geno-type | Age at sample | Time from SC | Time from T1D diagnosis | ICA, JDFU | Control Sample name | Gender | HLA-DQB1 geno-type | Age at sample/days |
|---|---|---|---|---|---|---|---|---|---|---|
| D14_1 | Male | 02, 0302 | 88 | −2135 | −3120 | 0 | C14_1 | Male | 02, 0302 | 97 |
| D14_2 | | | 1841 | −382 | −1367 | 0 | C14_2 | | | 1787 |
| D14_3 | | | 2055 | −168 | −1153 | 0 | C14_3 | | | 2045 |
| D14_4 | | | 2383 | 160 | −825 | 1 | C14_4 | | | 2417 |
| D14_5 | | | 2824 | 601 | −384 | 1 | C14_5 | | | 2827 |
| D14_6 | | | 2915 | 692 | −293 | 1 | C14_6 | | | 3009 |
| D14_7 | | | 3206 | 983 | −2 | 1 | C14_7 | | | 3184 |
| D15_1 | Male | 02, 0302 | 104 | −839 | −2927 | 0 | C15_1 | Male | 02, 0302 | 85 |
| D15_2 | | | 655 | −288 | −2376 | 0 | C15_2 | | | 638 |
| D15_3 | | | 746 | −197 | −2285 | 0 | C15_3 | | | 735 |
| D15_4 | | | 2105 | 1162 | −926 | 1 | C15_4 | | | 2148 |
| D15_5 | | | 2491 | 1548 | −540 | 1 | C15_5 | | | 2490 |
| D15_6 | | | 2636 | 1693 | −395 | 1 | C15_6 | | | 2668 |
| D16_1 | Female | 02, 0302 | 284 | −84 | −3366 | 0 | C16_1 | Female | 02, 0302 | 272 |
| D16_2 | | | 368 | 0 | −3282 | 0 | C16_2 | | | 359 |
| D16_3 | | | 2930 | 2562 | −720 | 1 | C16_3 | | | 2759 |
| D16_4 | | | 3112 | 2744 | −538 | 1 | C16_4 | | | 3122 |
| D16_5 | | | 3203 | 2835 | −447 | 1 | C16_5 | | | 3288 |
| D16_6 | | | 3650 | 3282 | 0 | 1 | C16_6 | | | 3645 |
| D17_1 | Female | 02, 0302 | 280 | −1560 | −2515 | 0 | C17_1 | Female | 02, 0302 | 259 |
| D17_2 | | | 1469 | −371 | −1326 | 0 | C17_2 | | | 1485 |
| D17_3 | | | 1644 | −196 | −1151 | 0 | C17_3 | | | 1641 |
| D17_4 | | | 1840 | 0 | −955 | 0 | C17_4 | | | 1856 |
| D17_5 | | | 1989 | 149 | −806 | 1 | C17_5 | | | 2015 |
| D17_6 | | | 2197 | 357 | −598 | 1 | C17_6 | | | 2198 |
| D17_7 | | | 2710 | 870 | −85 | 1 | C17_7 | | | 2739 |
| D18_1 | Male | 0302 | 368 | −99 | −4060 | 0 | C18_1 | Male | 0302 | 387 |
| D18_2 | | | 3133 | 2666 | −1295 | 1 | C18_2 | | | 3108 |
| D18_3 | | | 3304 | 2837 | −1124 | 1 | C18_3 | | | 3297 |
| D18_4 | | | 3513 | 3046 | −915 | 1 | C18_4 | | | 3485 |
| D18_5 | | | 4235 | 3768 | −193 | 1 | C18_5 | | | 4207 |
| D18_6 | | | 4332 | 3865 | −96 | 1 | C18_6 | | | 4396 |
| D19_1 | Female | 0302 | 116 | −355 | −3008 | 0 | C19_1 | Female | 0302 | 126 |
| D19_2 | | | 285 | −186 | −2839 | 0 | C19_2 | | | 279 |
| D19_3 | | | 374 | −97 | −2750 | 0 | C19_3 | | | 378 |
| D19_4 | | | 2418 | 1947 | −706 | 0 | C19_4 | | | 2378 |
| D19_5 | | | 2577 | 2106 | −547 | 0 | C19_5 | | | 2567 |
| D19_6 | | | 2747 | 2276 | −377 | 0 | C19_6 | | | 2742 |
| D19_7 | | | 2948 | 2477 | −176 | 1 | C19_7 | | | 2931 |

TABLE 3c

Label-free samples LFQ2

| Case Sample name | Gender | HLA-DQB1 geno-type | Age at sample | Time from SC | Time from T1D diagnosis | ICA, JDFU | Control Sample name | Gender | HLA-DQB1 geno-type | Age at sample/days |
|---|---|---|---|---|---|---|---|---|---|---|
| D20_1 | Male | *03:02, x | 179 | −736 | −2227 | 0 | C20_1 | Male | *03:02, x | 191 |
| D20_2 | | | 650 | −265 | −1756 | 0 | C20_2 | | | 638 |
| D20_3 | | | 748 | −167 | −1658 | 0 | C20_3 | | | 714 |
| D20_4 | | | 915 | 0 | −1491 | 1 | C20_4 | | | 910 |
| D20_5 | | | 1811 | 896 | −595 | 1 | C20_5 | | | 1816 |
| D20_6 | | | 2022 | 1107 | −384 | 1 | C20_6 | | | 1995 |
| D20_7 | | | 2210 | 1295 | −196 | 1 | C20_7 | | | 2191 |
| D20_8 | | | 2330 | 1415 | −76 | 1 | C20_8 | | | 2359 |
| D20_9 | | | 2406 | 1491 | 0 | 1 | C20_9 | | | 2557 |
| D21_1 | Male | *02, *03:02 | 89 | −1362 | −4477 | 0 | C21_1 | Male | *02, *03:02 | 91 |
| D21_2 | | | 1262 | −350 | −3465 | 0 | C21_2 | | | 1282 |
| D21_3 | | | 1101 | −189 | −3304 | 0 | C21_3 | | | 1449 |
| D21_4 | | | 1451 | 0 | −3115 | 1 | C21_4 | | | 3836 |
| D21_5 | | | 3875 | 2424 | −691 | 1 | C21_5 | | | 4024 |
| D21_6 | | | 4049 | 2598 | −517 | 1 | C21_6 | | | 4200 |
| D21_7 | | | 4254 | 2803 | −312 | 1 | C21_7 | | | 4382 |
| D21_8 | | | 4344 | 2893 | −222 | 1 | C21_8 | | | 4564 |
| D21_9 | | | 4525 | 3074 | −41 | 1 | | | | |
| D22_1 | Female | *02, *03:02 | 94 | −642 | −2736 | 0 | C22_1 | Female | *02, *03:02 | 187 |
| D22_2 | | | 183 | −553 | −2647 | 0 | C22_2 | | | 550 |
| D22_3 | | | 561 | −175 | −2269 | 0 | C22_3 | | | 647 |

TABLE 3c-continued

Label-free samples LFQ2

| Case Sample name | Gender | HLA-DQB1 genotype | Age at sample | Time from SC | Time from T1D diagnosis | ICA, JDFU | Control Sample name | Gender | HLA-DQB1 genotype | Age at sample/days |
|---|---|---|---|---|---|---|---|---|---|---|
| D22_4 | | | 645 | −91 | −2185 | 0 | C22_4 | | | 733 |
| D22_5 | | | 736 | 0 | −2094 | 1 | C22_5 | | | 2189 |
| D22_6 | | | 2220 | 1484 | −610 | 1 | C22_6 | | | 2385 |
| D22_7 | | | 2416 | 1680 | −414 | 1 | C22_7 | | | 2543 |
| D22_8 | | | 2570 | 1834 | −260 | 1 | C22_8 | | | 2748 |
| D22_9 | | | 2753 | 2017 | −77 | 1 | C22_9 | | | 2915 |
| D22_10 | | | 2829 | 2093 | −1 | 1 | | | | |
| D23_1 | Female | *02, *03:02 | 96.00 | −283 | −1205 | 0 | C23_1 | Female | *02, *03:02 | 122 |
| D23_2 | | | 181.00 | −198 | −1120 | 0 | C23_2 | | | 278 |
| D23_3 | | | 281.00 | −98 | −1020 | 0 | C23_3 | | | 466 |
| D23_4 | | | 482.00 | 103 | −819 | 1 | C23_4 | | | 586 |
| D23_5 | | | 580.00 | 201 | −721 | 1 | C23_5 | | | 1111 |
| D23_6 | | | 1104.00 | 725 | −197 | 1 | C23_6 | | | 1306 |
| D23_7 | | | 1301.00 | 922 | 0 | 1 | C23_7 | | | 1663 |
| D24_1 | Female | *02, *03:02 | 97.00 | −358.00 | −3032.00 | 0 | C24_1 | Female | *02, *03:02 | 87 |
| D24_2 | | | 293.00 | −162.00 | −2836.00 | 0 | C24_2 | | | 275 |
| D24_3 | | | 371.00 | −84.00 | −2758.00 | 0 | C24_3 | | | 369 |
| D24_4 | | | 455.00 | 0.00 | −2674.00 | 1 | C24_4 | | | 452 |
| D24_5 | | | 2491.00 | 2036.00 | −638.00 | 1 | C24_5 | | | 2524 |
| D24_6 | | | 2731.00 | 2276.00 | −398.00 | 1 | C24_6 | | | 2699 |
| D24_7 | | | 2834.00 | 2379.00 | −295.00 | 1 | C24_7 | | | 2888 |
| D24_8 | | | 3032.00 | 2577.00 | −97.00 | 1 | C24_8 | | | 3063 |
| D24_9 | | | 3129.00 | 2674.00 | 0.00 | 1 | C24_9 | | | 3247 |
| D25_1 | Female | *02, *03:02 | 184.00 | ####### | −3224.00 | 0 | C25_1 | Female | *02, *03:02 | 277 |
| D25_2 | | | 279.00 | ####### | −3129.00 | 0 | C25_2 | | | 1495 |
| D25_3 | | | 1479.00 | −902.00 | −1929.00 | 0 | C25_3 | | | 1831 |
| D25_4 | | | 1847.00 | −534.00 | −1561.00 | 0 | C25_4 | | | 2034 |
| D25_5 | | | 2017.00 | −364.00 | −1391.00 | 0 | C25_5 | | | 2162 |
| D25_6 | | | 2220.00 | −161.00 | −1188.00 | 0 | C25_6 | | | 2517 |
| D25_7 | | | 2577.00 | 196.00 | −831.00 | 1 | C25_7 | | | 2706 |
| D25_8 | | | 2745.00 | 364.00 | −663.00 | 1 | C25_8 | | | 2874 |
| D25_9 | | | 3398.00 | 1017.00 | −10.00 | 1 | | | | |
| D26_1 | Female | *02, *03:02 | 88.00 | −699.00 | −3280 | 0 | C26_1 | Female | *02, *03:02 | 71 |
| D26_2 | | | 467.00 | −320.00 | −2901 | 0 | C26_2 | | | 450 |
| D26_3 | | | 555.00 | −232.00 | −2813 | 0 | C26_3 | | | 546 |
| D26_4 | | | 3074.00 | 2287.00 | −294 | 1 | C26_4 | | | 3089 |
| D26_5 | | | 3140.00 | 2353.00 | −228 | 1 | C26_5 | | | 3283 |
| D26_6 | | | 3224.00 | 2437.00 | −144 | 1 | C26_6 | | | 3446 |
| D26_7 | | | 3326.00 | 2539.00 | −42 | 1 | C26_7 | | | 3656 |
| D27_1 | Male | *03:02, x | 101.00 | −980.00 | −1450.00 | 0 | C27_1 | Male | *03:02, x | 97 |
| D27_2 | | | 738.00 | −343.00 | −813.00 | 0 | C27_2 | | | 705 |
| D27_3 | | | 901.00 | −180.00 | −650.00 | 0 | C27_3 | | | 1089 |
| D27_4 | | | 1091.00 | 10.00 | −460.00 | 1 | C27_4 | | | 1384 |
| D27_5 | | | 1194.00 | 113.00 | −357.00 | 1 | C27_5 | | | 1559 |
| D27_6 | | | 1277.00 | 196.00 | −274.00 | 1 | C27_6 | | | 1740 |
| D27_7 | | | 1369.00 | 288.00 | −182.00 | 1 | | | | |
| D27_8 | | | 1465.00 | 384.00 | −86.00 | 1 | | | | |
| D28_1 | Male | *02, *03:02 | 188.00 | −301.00 | −1184.00 | 0 | C28_1 | Male | *02, *03:02 | 169 |
| D28_2 | | | 307.00 | −182.00 | −1065.00 | 0 | C28_2 | | | 267 |
| D28_3 | | | 405.00 | −84.00 | −967.00 | 0 | C28_3 | | | 454 |
| D28_4 | | | 656.00 | 167.00 | −716.00 | 1 | C28_4 | | | 677 |
| D28_5 | | | 774.00 | 285.00 | −598.00 | 1 | C28_5 | | | 740 |
| D28_6 | | | 1153.00 | 664.00 | −219.00 | 1 | C28_6 | | | 915 |
| D28_7 | | | 1244.00 | 755.00 | −128.00 | 1 | C28_7 | | | 1104 |
| D28_8 | | | 1364.00 | 875.00 | −8.00 | 1 | C28_8 | | | 1280 |

Sample Comparisons

Paired Samples

The comparisons for the samples were mostly paired within a time window of 60 days, with but a few exceptions where a later sample was used. The samples where no pairing could be made were only used to gain an overview in the clustering of the expression profiles. For the analysis of selected time points the following grouping was made (based on the use of the paired case/control ratios) according to the ages and time intervals in Table 3a and Table 3b: The samples were grouped on the basis of collection time
i) 3 to 6 months pre-seroconversion;
ii) 9 to 12 months pre-seroconversion;
iii) 3 to 6 months pre-diagnosis;
iv) 9 to 12 months pre-diagnosis;
v) 15 to 18 months pre-diagnosis;
vi) Throughout the 18 months pre-diagnosis Example 3. Results The iTRAQ measurements detailed on average the quantitative comparison of 220 proteins, and in total 658 proteins were identified and quantified with two or more unique peptides. In comparison to reference concentrations and after excluding depletion targets these spanned a range of estimated concentrations of six orders of magnitude. With the analyses using a label free approach, 261 proteins were consistently detected and quantified with more than one unique peptide and spanned a similar dynamic range of detection. There were 248 proteins common to the two techniques.

With similar analysis of the age matched post seroconversion data, several proteins were distinguished with a lower relative abundance, including SHBG, ADIPO, THBG, APOC4, APOC2, IBP2, APOC1, and APOC3 (FDR<5%, Table 4).

TABLE 4

Serum proteins detected at different levels between children progressing to type 1 diabetes and their matched controls

| ID | Entry name | Protein names | col | q-value |
|---|---|---|---|---|
| P55056 | APOC4 | Apolipoprotein C-IV | a−, b−, d−, e−, g−, h−, j− | 0.000 |
| P02655 | APOC2 | Apolipoprotein C-II | a−, b−, d−, e−, g−, h−, j− | 0.001 |
| P18065 | IBP2 | Insulin-like growth factor-binding protein 2 | d−, e−, j−, g− | 0.009 |
| P11226 | MBL2 | Mannose-binding protein C | a−, e−, g−, j− | 0.011 |
| P07737 | PROF1 | Profilin-1 | b+, c+, d+, h+ | 0.000 |
| P04278 | SHBG | Sex hormone-binding globulin | a−, e−, g−, j− | 0.002 |
| P02654 | APOC1 | Apolipoprotein C-I | a−, e−, j−, g− | 0.031 |
| P02656 | APOC3 | Apolipoprotein C-III | a−, j−, g− | 0.013 |
| Q96KN2 | CNDP1 | Beta-Ala-His dipeptidase | a+, e+, j+ | 0.017 |
| P21333 | FLNA | Filamin-A | a+, d+, h+ | 0.000 |
| P00740 | FA9 | Coagulation factor IX | g+, j+ | 0.004 |
| P02751 | FINC | Fibronectin | b−, g+ | 0.009 |
| P05154 | IPSP | Plasma serine protease inhibitor | g+, j+ | 0.007 |
| P12955 | PEPD | Xaa-Pro dipeptidase | d−, h− | 0.003 |
| P32119 | PRDX2 | Peroxiredoxin-2 | h−, e+ | 0.005 |
| P37802 | TAGL2 | Transgelin-2 | d+, h+ | 0.000 |
| Q15848 | ADIPO | Adiponectin | e− | 0.000 |
| P08519 | APOA | Apolipoprotein(a) | h− | 0.000 |
| Q15582 | BGH3 | Transforming growth factor-beta-induced protein ig-h3 | e− | 0.019 |
| P43251 | BTD | Biotinidase | g+ | 0.017 |
| P04003 | C4BPA | C4b-binding protein alpha chain | e+ | 0.013 |
| P02748 | CO9 | Complement component C9 | e+ | 0.010 |
| P09172 | DOPO | Dopamine beta-hydroxylase | e+ | 0.000 |
| Q9NPH3 | IL1AP | Interleukin-1 receptor accessory protein | c+ | 0.030 |
| Q08380 | LG3BP | Galectin-3-binding protein | e+ | 0.012 |
| P43121 | MUC18 | Cell surface glycoprotein MUC18 | d− | 0.049 |
| Q6UXB8 | PI16 | Peptidase inhibitor 16 | e− | 0.018 |
| Q15063 | POSTN | Periostin | e− | 0.005 |
| P06702 | S10A9 | Protein S100-A9 | i− | 0.001 |
| P02743 | SAMP | Serum amyloid P-component | e+ | 0.049 |
| P35443 | TSP4 | Thrombospondin-4 | d− | 0.043 |
| Q9UK55 | ZPI | Protein Z-dependent protease inhibitor | i+ | 0.036 | a) Throughout, n = 28,
b) Pre-seroconversion (PS), n = 23,
c) 9 to 12 months PS,
d) 3 to 6 months PS,
e) Post seroconversion and <1.5 year pre-diagnosis (PD), n = 28,
f) 15 to 18 months PD, n = 28,
g) 3 to 6 months PD, n = 20,
h) 3 to 12 months PS.
i) at diagnosis,
j) Post seroconversion (all)

Differences Between the Serum Proteomes of Children Who Developed T1D and their Age Matched Controls For the subjects considered in this study, the children who developed T1D had lower levels of SHBG, APOC4, APOC2, and APOC1 than their age-matched healthy controls (FDR<3%) (Table 3).

In samples before seroconversion, lower levels of APOC4 and APOC2 and APOA were apparent in children developing type 1 diabetes than in their controls. Similarly, specific consideration of the samples 3 to 6 months prior to seroconversion was consistent with the lower levels of both IBP2, TSP4, APOC2 and APOC4, as well as a larger relative abundance of PROF1, FLNA, and TAGL2.

Longitudinal Changes in the Serum Proteome of Children En Route to T1D

With the analysis of protein abundance ratios there were no significant correlations observed between the case-control ratios with time towards diagnosis. On the contrary, the case and control reference correlations gave a much clearer indication of the longitudinal changes in the serum proteome in both case and control. Distinct from the correlated proteins observed with both the case and control children (>0.4, FDR<0.05) were changes in the abundance of 26 proteins (14 increased and 12 decreased, FDR<5%, Table 5). This included proteins reported in Table 4, emphasizing their utility in assessing advancement of the disease.

TABLE 5

Longitudinal changes in serum proteins specific to T1D-developing children

| Protein names | Entry name | Entry | Average Unique Peptides iTRAQ | Average Unique Peptides Label Free | Average % Sequence Coverage* | Correlation coefficient (Spearman) |
|---|---|---|---|---|---|---|
| Fetuin-B | FETUB | Q9UGM5 | 18 | 7 | 30 | 0.63 |
| Serum amyloid P-component | SAMP | P02743 | 32 | 9 | 37 | 0.51 |
| Clusterin | CLUS | P10909 | 70 | 35 | 43 | 0.50 |
| C4b-binding protein alpha chain | C4BPA | P04003 | 21 | 11 | 24 | 0.49 |
| C4b-binding protein beta chain | C4BPB | P20851 | 5 | 2 | 20 | 0.48 |
| Complement factor I | CFAI | P05156 | 50 | 44 | 48 | 0.45 |
| Inter-alpha-trypsin inhibitor heavy chain H4 | ITIH4 | Q14624 | 251 | 92 | 63 | 0.44 |
| Apolipoprotein C-IV | APOC4 | P55056 | 4 | 6 | 22 | 0.44 |
| Insulin-like growth factor-binding protein 3 | IBP3 | P17936 | 12 | 13 | 27 | |
| Serum amyloid A-4 protein | SAA4 | P35542 | 5 | 10 | 22 | 0.43 |
| Complement component C8 alpha chain | CO8A | P07357 | 51 | 35 | 38 | 0.43 |
| Complement C1q subcomponent subunit B | C1QB | P02746 | 27 | 17 | 29 | 0.42 |
| Hyaluronan-binding protein 2 | HABP2 | Q14520 | 20 | 12 | 26 | 0.40 |
| Complement component C8 gamma chain | CO8G | P07360 | 28 | 7 | 58 | 0.40 |
| Transforming growth factor-beta-induced protein ig-h3 | BGH3 | Q15582 | 17 | 10 | 24 | −0.41 |
| Ectonucleotide pyrophosphatase/phosphodiesterase family member 2 | ENPP2 | Q13822 | 11 | 4 | 12 | −0.41 |
| Poliovirus receptor | PVR | P15151 | 5 | 4 | 8 | −0.42 |
| Vinculin | VINC | P18206 | 6 | 3 | 6 | −0.42 |
| N-acetylmuramoyl-L-alanine amidase | PGRP2 | Q96PD5 | 61 | 31 | 50 | −0.42 |
| Contactin-1 | CNTN1 | Q12860 | 8 | 1 | 9 | −0.43 |
| L-lactate dehydrogenase B chain 46) | LDHB | P07195 | 9 | 2 | 24 | −0.46 |
| Extracellular superoxide dismutase [Cu-Zn] | SODE | P08294 | 7 | 4 | 28 | −0.48 |
| Apolipoprotein A-IV | APOA4 | P06727 | 189 | 97 | 74 | −0.54 |
| Adiponectin | ADIPO | Q15848 | 13 | 3 | 33 | −0.54 |
| Neural cell adhesion molecule 1 | NCAM1 | P13591 | 13 | 5 | 17 | −0.60 |
| Insulin-like growth factor-binding protein 2 | IBP2 | P18065 | 6 | 6 | 19 | −0.64 |

A subset of proteins was identified were the absolute Spearman's correlation coefficient was greater than 0.4 (FDR<0.05) and not observed at or above these thresholds in the control subjects. The analysis was based on the changes observed in eleven children representing the samples before and after seroconversion (D1, D4, D5, D9, D10, D11, D12, D14, D15, D17, D19). The functional enrichment for these proteins is show in Table 6. Notably included in this list were the proteins ADIPO and IBP2, which were also detected as differentially abundant in the rank product analyses. The temporal change of these proteins could be used to assess increased risk, particularly in seroconverted subjects.

TABLE 6

GO annotations enriched in proteins increasing in the children, who progressed to type 1 diabetes

| Term | P-Value | Proteins | FDR |
|---|---|---|---|
| GO:0002526 acute inflammatory response | 3.8E−04 | P07357, Q14624, P04003, P05156, P02746, P20851, P10909, P07360, P02743, P35542 | 0.3 |
| GO:0019724 B cell mediated immunity | .6E−04 | P07357, P04003, P05156, P02746, P20851, P10909, P07360 | 1.0 |
| GO:0006958 complement activation, classical pathway | 8.6E−04 | P07357, P04003, P05156, P02746, P20851, P10909, P07360 | 1.0 |
| GO:0016064 immunoglobulin mediated immune response | 8.6E−04 | P07357, P04003, P05156, P02746, P20851, P10909, P07360 | 1.0 |
| GO:0002455 humoral immune response mediated by circulating immunoglobulin | 8.6E−04 | P07357, P04003, P05156, P02746, P20851, P10909, P07360 | 1.0 |
| GO:0006954 inflammatory response | 0.0010 | P07357, Q14624, P04003, P05156, P02746, P20851, P10909, P07360, P02743, P35542 | 1.3 |

TABLE 6-continued

GO annotations enriched in proteins increasing in the children, who progressed to type 1 diabetes

| Term | P-Value | Proteins | FDR |
| --- | --- | --- | --- |
| Complement pathway | 0.0013 | P07357, P04003, P05156, P02746, P20851, P10909, P07360 | 1.3 |
| GO:0002250 adaptive immune response | 0.0014 | P07357, P04003, P05156, P02746, P20851, P10909, P07360 | 1.7 |
| GO:0002449 lymphocyte mediated immunity | 0.0014 | P07357, P04003, P05156, P02746, P20851, P10909, P07360 | 1.7 |
| GO:0002460 adaptive immune response based on somatic recombination of immune receptors built from immunoglobulin superfamily domains | 0.0014 | P07357, P04003, P05156, P02746, P20851, P10909, P07360 | 1.7 |
| GO:0002443 leukocyte mediated immunity | 0.0018 | P07357, P04003, P05156, P02746, P20851, P10909, P07360 | 2.1 |
| GO:0006952 defense response | 0.0032 | P07357, Q14624, P04003, P05156, P02746, P20851, P10909, P07360, P02743, P35542 | 3.8 |
| Innate immunity | .0039 | P07357, P04003, P05156, P02746, P20851, P10909, P07360 | 3.8 |
| GO:0006959 humoral immune response | 0.0041 | P07357, P04003, P05156, P02746, P20851, P10909, P07360 | 4.8 |
| GO:0002541 activation of plasma proteins involved in acute inflammatory response | 0.0041 | P07357, P04003, P05156, P02746, P20851, P10909, P07360 | 4.8 |
| GO:0002253 activation of immune response | 0.0041 | P07357, P04003, P05156, P02746, P20851, P10909, P07360 | 4.8 |
| GO:0006956 complement activation | 0.0041 | P07357, P04003, P05156, P02746, P20851, P10909, P07360 | 4.8 |

Enrichment was calculated for proteins with an absolute Spearman's correlation coefficient of greater than 0.4 (FDR<0.05) that were not observed at or above these thresholds in the control subjects. A background of the 208 proteins detected for these analyses was used in the enrichment analysis. The protein names and detection details are indicated in Table 3.

Serum Proteomics Classification of the T1D-Developing Subjects

The top scoring pairs (TSP) method was applied to identify whether combinations of the quantified proteins could classify the samples and subjects. The leave-one-out method was used for cross validation.

TSP analysis for the subjects of iTRAQ and LFQ1 in which APOC4 was quantified (16 of 19) classified the children progressing to type 1 diabetes at a success rate of 91%; the area under the curve was 0.89. The classification was based on the combination of the relative levels of APOC4 and AFAM, which were lower and higher than in the controls, respectively (FIGS. 4A and 5A).

TSP analysis for the LFQ2 subjects demonstrated that SHBG in combination with other proteins gave good classification of the subjects throughout the time series (up to 94% success rate). Analysis of the label free data alone (LFQ1 and LFQ2) revealed that the combination of SHBG and BTD provided an AUC of 0.85 for the post seroconversion data, and 0.77 pre-seroconversion.

For the collected data SHBG provided areas under of the curve for received operator curves combinations of these markers were in the order of 0.75 to 0.81. These combinations included higher levels of the following throughout: THBG, CO8G, BTD, CO5, and ZPI.

Profilin 1 (PFN1) has been associated with inflammation and insulin resistance, and notably significant differences were detected both before and after seroconversion (decreasing in the latter case). Notably the a peak in profilin 1 was observed before seroconversion and pathway analysis of the differentially abundant proteins detected at this time period indicated functionally related proteins (FIG. 7). Indeed ROC characteristics of the combination of PROF1 and FLNA improved the AUC to 0.88. Collectively these findings reflect metabolic differences and changes preceding the diagnosis of type 1 diabetes.

The invention claimed is:

1. A method of determining an individual at risk of and/or progression towards Type 1 Diabetes (T1D), the method comprising:
    a) determining a protein marker profile in a sample obtained from the individual, said profile comprising afamin (AFAM) and apolipoprotein C-IV (APOC4);
    b) comparing the determined protein marker profile of APOC4 and AFAM of the individual with that of a corresponding control profile of APOC4 and AFAM in a control sample from a control individual or a pool of control individuals,
    c) responsive to the comparison, determining the risk of and/or progression towards T1D in the individual, wherein a lower and a higher level of APOC4 and AFAM, respectively, in the sample obtained from the individual as compared to the levels of APOC4 and AFAM in the control sample indicates that the individual is at risk of and/or progression towards T1D, and
    d) providing a treatment or dietary change to the individual to prevent T1D development.

2. The method according to claim 1, wherein the individual is determined at risk of and/or progressing towards T1D prior to seroconversion in the individual.

3. The method according to claim 1, wherein the individual has a Human Leukocyte Antigen-conferred (HLA-conferred) risk of T1D.

4. The method according to claim 1, further comprising: determining one or more protein markers selected from the group consisting of sex hormone-binding globulin (SHBG), adiponectin (ADIPO), thyroxine-binding globulin (THBG), apolipoprotein C-II (APOC2), insulin-like growth factor-binding protein 2 (IBP2), apolipoprotein C-I (APOC1), apolipoprotein C-III (APOC3), fetuin-B (FETUB), serum amyloid P-component (SAMP), clusterin (CLUS), C4b-binding protein alpha chain (C4BPA), C4b-BIRCH, binding protein beta chain (C4BPB), complement factor I (CFAI), inter-alpha-trypsin inhibitor heavy chain H4 (ITIH4), insulin-like growth factor-binding protein 3 (IBP3), Serum amyloid A4 protein (SAA4), complement component C8 alpha chain (CO8A), complement C1q subcomponent subunit B (C1QB), hyaluronan-binding protein 2 (HABP2), complement component C8 gamma chain (CO8G), transforming growth factor-beta-induced protein ig-h3 (BGH3), ectonucleotide pyrophosphatase/phosphodiesterase family member 2 (ENPP2), poliovirus receptor (PVR), vinculin (VINC), N-acetylmuramoyl-L-alanine amidase (PGRP2), contactin-1 (CNTN1), L-lactate dehydrogenase B chain 46 (LDHB), extracellular superoxide dismutase [Cu—Zn] (SODE), apolipoprotein A-IV (APOA4), neural cell adhesion and molecule 1 (NCAM1), and comparing the determined one or more protein markers with that of corresponding control markers, wherein a lower level of SHBG, ADIPO, THBG, APOC2, APOC1, APOC3, BGH3, ENPP2, PVR, VINC, PGRP2, CNTN1, LDHB, SODE, APOA4, NCAM1, or IBP2 in the sample obtained from the individual as compared to the levels in the control sample indicates that the individual is at risk of and/or progression towards T1D, and wherein a higher level of FETUB, SAMP, CLUS, C4BPA, C4BPB, CFAI, ITIH4, IBP3, SAA4, CO8A, C1QB, HABP2, or CO8G in the sample obtained from the individual as compared to the levels in the control sample indicates that the individual is at risk of and/or progression towards T1D.

5. The method according to claim 1, wherein said a)-c) steps are performed by a processor of a computing device.

6. The method according to claim 1, wherein said sample is selected from the group consisting of a whole blood sample, a plasma sample, a serum sample, a sample comprising purified blood cells, a tissue sample, and a urine sample.

\* \* \* \* \*